(12) United States Patent
Wanders

(10) Patent No.: US 9,999,498 B2
(45) Date of Patent: Jun. 19, 2018

(54) INTRAOCULAR LENS STRUCTURE

(71) Applicant: OCULENTIS HOLDING B.V., Eerbeek (NL)

(72) Inventor: Bernardus Franciscus Maria Wanders, Angerlo (NL)

(73) Assignee: OCULENTIS HOLDING B.V., Eerbeek (NL)

( * ) Notice: Subject to any disclaimer, the term of this patent is extended or adjusted under 35 U.S.C. 154(b) by 0 days. days.

(21) Appl. No.: 14/909,078

(22) PCT Filed: Jul. 28, 2014

(86) PCT No.: PCT/NL2014/050519
§ 371 (c)(1),
(2) Date: Jan. 29, 2016

(87) PCT Pub. No.: WO2015/016705
PCT Pub. Date: Feb. 5, 2015

(65) Prior Publication Data
US 2016/0184088 A1    Jun. 30, 2016

(30) Foreign Application Priority Data

Jul. 29, 2013 (NL) ...................................... 2011235
Sep. 19, 2013 (NL) ...................................... 2011475
(Continued)

(51) Int. Cl.
A61F 2/16 (2006.01)
A61F 9/007 (2006.01)
A61F 2/00 (2006.01)

(52) U.S. Cl.
CPC .............. *A61F 2/16* (2013.01); *A61F 2/1601* (2015.04); *A61F 9/007* (2013.01);
(Continued)

(58) Field of Classification Search
CPC .... A61F 2/16; A61F 2/1601; A61F 2002/009; A61F 2002/1689
See application file for complete search history.

(56) References Cited

U.S. PATENT DOCUMENTS 5,697,973 A * 12/1997 Peyman .................... A61F 2/16
623/6.26

FOREIGN PATENT DOCUMENTS

EP    0916320 A2    5/1999
EP    2039324 A1    3/2009
(Continued)

OTHER PUBLICATIONS

S Krag et al: "Biomechanical characteristics of the human anterior lens capsule in relation to age", Investigative Ophthalmology & Visual Science—IOVS, vol. 38, No. 2, Feb. 1, 1997 (Feb. 1, 1997), pp. 357-363, XP055109706, US ISSN: 0146-0404 the whole document.

(Continued)

*Primary Examiner* — David H Willse
*Assistant Examiner* — Tiffany Shipmon
(74) *Attorney, Agent, or Firm* — AEON Law, PLLC; Adam Phillip; Manasi Vakil

(57) ABSTRACT

The invention provides an intra ocular lens structure (IOL) for placement in the capsular bag and securing the IOL in an opening in an anterior part of a capsular bag, with an anterior capsular bag flap surrounding said opening, said IOL having an anterior side which in use when the IOL is implanted in an eye is directed towards a cornea of the eye, and a posterior side which in use when the IOL is implanted in an eye is directed towards a retina of the eye, said IOL comprising an optical structure, at least two posterior supports for when the IOL is implanted in the capsular bag residing in the capsular bag extending away from said optical structure, said posterior supports adapted for in use providing support surfaces for a posterior surface of an anterior capsular bag flap, and at least two anterior supports (Continued)

for when the IOL is implanted in the capsular bag residing outside the capsular bag extending away from said optical structure, said anterior supports adapted for in use providing support surfaces for an anterior surface of an anterior capsular bag flap.

16 Claims, 15 Drawing Sheets

(30) Foreign Application Priority Data

Oct. 4, 2013 (NL) ...................................... 2011562
Apr. 18, 2014 (NL) ...................................... 2012659

(52) U.S. Cl.
CPC . *A61F 2002/009* (2013.01); *A61F 2002/1689* (2013.01); *A61F 2002/16901* (2015.04)

(56) References Cited

FOREIGN PATENT DOCUMENTS

| | | |
|---|---|---|
| EP | 2422746 A1 | 2/2012 |
| WO | 02/09619 A2 | 2/2002 |

OTHER PUBLICATIONS

Krag S et al: "Mechanical properties of the human posterior lens capsule", Investigative Ophthalmology & Visual Science—IOVS, vol. 44, No. 2, Feb. 1, 2003 (Feb. 1, 2003), pp. 691-696, XP002292421, US ISSN: 0146-0404, DOI: 10.1167/IOVS.02-0096 the whole document.

* cited by examiner

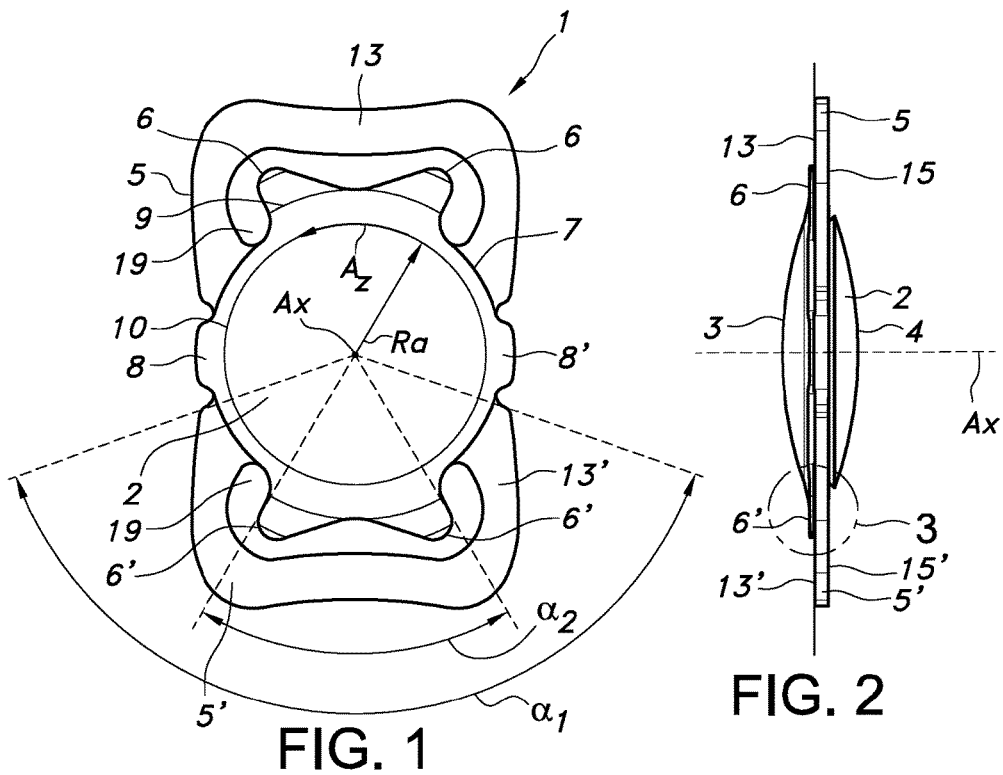
FIG. 1
FIG. 2
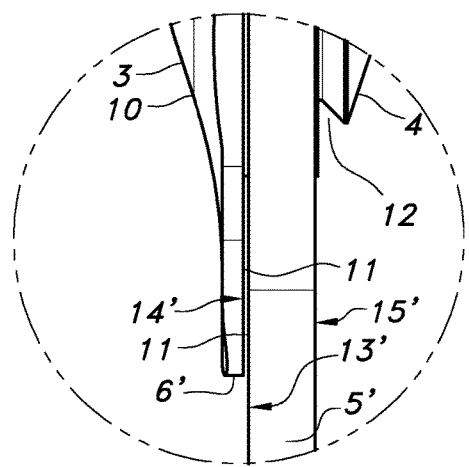
FIG. 3

INTRAOCULAR LENS STRUCTURE

FIELD OF THE INVENTION

The invention relates to an intraocular lens structure (IOL), and a method for inserting such an IOL.

BACKGROUND OF THE INVENTION

In modern cataract procedures, also called extracapsular cataract extraction, a hole is cut in the anterior capsular bag. This may be done using laser devices. Subsequently, the natural lens is removed. In the remaining parts of the capsular bag, in many suggested procedures an IOL is placed. The IOL more or less maintains its position in the empty bag.

Usually, an IOL is provided with haptics. These haptics extend radially from a lens of an IOL. After implanting an IOL, these haptics usually engage the inside circumference of the remaining capsular bag part in order to more or less keep the optics, for instance a lens, of the IOL centred and positioned in the capsular bag.

For improving fixation of the position of an IOL, many designs were proposed. U.S. Pat. No. 6,027,531 describes in its abstract "An intraocular lens for use in extracapsular cataract extraction has a haptic pa[r]t that surrounds the optical pa[r]t of the lens and further contains a groove of such shape to accommodate the anterior and posterior capsules of the lens bag after anterior capsulorhexis, extracapsular cataract extraction and posterior capsulorhexis. The lens is preferably inserted in a calibrated, circular and continuous combined anterior and posterior capsulorhexis, slightly smaller than the inner circumference of the groove as to induce a stretching of the rims of the capsular openings. This new approach is believed to prevent the appearance of secondary opacification of the capsules, allows a very stable fixation of the intraocular lens and ensures a tight separation between the anterior and posterior segment of the eye. This new principle of insertion is called the bag-in-the-lens technique, in contrast with the classical lens in-the-bag technique.". Placement of this IOL requires skills and the capsular bag may get damaged. If after insertion the capsular bag ruptures, the IOL will not maintain its position.

In U.S. Pat. No. 6,881,225, an intraocular lens structure for reducing complications is described. According to the abstract, the intraocular lens structure comprises an optic, a support and a closing fixture. The closing fixture is a groove or a valley formed on the side portion of the optic of the intraocular lens. The valley is formed by the optic and a protrusion projecting posteriorly from the optic. The groove or the valley in the optic is made engaged with the posterior capsular opening generally over the entire circumference of the groove or the valley to close the opening of the posterior capsule. Like most of the current IOL structures, the structure also uses its haptics for keeping the structure in the capsular bag. The groove holds the posterior part of the capsular bag.

U.S. Pat. No. 5,171,320 describes in its abstract an intraocular lens system adapted to be implanted within a generally circular opening in an anterior wall of the capsular bag which normally contains the crystalline lens of an eye. The intraocular lens system includes a lens body having an annular groove which is formed in a peripheral portion thereof in a plane substantially perpendicular to an optical axis of the lens body. The lens body includes an optically effective portion located radially inside the annular groove, and an anterior lens portion and a posterior lens portion located on respective anterior and posterior sides of the annular groove. The intraocular lens system is secured in position within the circular opening such that an annular flap portion of the capsular bag which surrounds the circular opening is accommodated within the annular groove in the lens body.

EP2422746 discloses according to its abstract an intraocular implant for placement in the eye, e.g. as part of a cataract operation or crystalline lens extraction refractive operation, has at a peripheral portion of the implant a groove which engages with the lip of a single capsulotomy only formed in the lens capsule of the eye. The implant will normally be a lens, but may instead be a bung or plug for occluding an opening made in the capsule. The groove may be a continuous groove around the periphery of the implant, or there may be a series of individual spaced-apart grooves formed as projections protruding from the periphery. Instead of a single groove, a pair of axially spaced-apart grooves may be provided, which engage with respective capsulotomies formed in an anterior and a posterior part of the capsule. The posterior groove is preferably of a smaller mean diameter than the anterior groove. The description shows an embodiment with "a series of projections projecting from the circumference of the lens portion", referring to very specific embodiments in the drawings.

SUMMARY OF THE INVENTION

A disadvantage of prior art is that placement of the IOL may be very difficult, with a high chance of damaging the capsular bag during the medical procedure, or may get damaged after the IOL is placed, or that there remains room for improvement.

Hence, it is an aspect of the invention to provide an alternative IOL, which preferably further at least partly obviates one or more of above-described drawbacks. In particular, the IOL of the invention allows proper and straightforward placement. Alternatively or additionally, it induces less damage to the capsular bag and allows secure positioning.

The invention provides an intra ocular lens structure (IOL) for placement in the capsular bag and securing the IOL in an opening in an anterior part of a capsular bag, with an anterior capsular bag flap surrounding said opening, said IOL having an anterior side which in use when the IOL is implanted in capsular bag of an eye is directed towards a cornea of the eye, and a posterior side which in use when the IOL is implanted in an eye is directed towards a retina of the eye. The IOL may comprises an optical structure comprising a perimeter. The IOL may furthermore comprise at least two posterior supports, coupled to and extending away from said perimeter of said optical structure. The posterior supports are provided for in use providing support surfaces for engaging a posterior surface of an anterior capsular bag flap. The posterior supports in use reside inside the capsular bag when the IOL is implanted in the capsular bag.

The IOL may further comprise at least two anterior supports, coupled to and extending from said perimeter of said optical structure, for in use residing outside the capsular bag and extending away from said optical structure. The anterior supports are adapted for in use providing support surfaces for engaging an anterior surface of an anterior capsular bag flap.

In an embodiment, a posterior plane defined by the support surfaces of the posterior supports and an anterior plane defined by the support surfaces of the anterior supports. These planes are adapted for in use being spaced apart at a distance adapted for holding an anterior capsular bag flap between them for securing the IOL in said opening.

It was found that due to the geometry and limited depth (approx. 0.2 mm) of prior art circumferential groove in known IOL's, the anterior capsular bag flap could easily escape from that groove resulting in IOL dislocation. Furthermore, the rotation stability of the lens structure may not optimal due to the prior art groove's geometry The IOL can be inserted into the capsular bag. The anterior and posterior supports allow fixing the IOL with its optical structure aligned with an opening, in particular an aperture or orifice, in a capsular bag.

The terms "anterior" and "posterior" relate to an arrangement of features relative to the propagation of the light into the eye. Thus, light enters through the cornea and passes the iris through the pupil. Cornea and iris are here considered anterior parts of the eye. Subsequently, the light propagates to the retina that is located in the posterior part of the eye.

The axis of an eye can be the optical axis, or can be the visual axis, the line of sight, or the pupillary axis.

An eye has a capsular bag that usually holds the natural lens. In conditions where that natural lens needs to be removed, an empty capsular bag remains. Usually, for removal of the natural lens, first an opening is made in the anterior part of the capsular bag. Part of the capsular bag membrane is removed. It leaves a through hole surrounded by a peripheral edge defining the perimeter. Such an opening can for instance be circular or elliptic. The anterior membrane of the capsular bag is thus provided with an aperture, providing an orifice that gives access to the capsular bag.

The part of the capsular bag that is closest to the cornea is here also referred to as the anterior capsular bag part. The remaining anterior capsular bag part that surrounds the mentioned opening is referred to as the anterior capsular bag flap. It can also be seen as a ring of capsular bag membrane.

The capsular bag also has a posterior part. That is the part of the capsular bag that is closest to the retina. The average capsular bag thickness is between 4 and 9 microns for the posterior capsular bag part and between 10 to 20 microns for the anterior capsular bag part.

In a procedure for removal of the natural lens, the opening in the anterior capsular bag can be made using a laser cutting device. This procedure for making the opening in the capsular bag is also referred to as capsulotomy. This laser-assisted procedure allows a very accurate positioning and shape of the opening in the capsular bag. Furthermore, after removal of the natural lens, it is possible to subsequently make an opening in the posterior part of the capsular bag, the posterior opening. This may prevent post operative posterior capsule opacification. These two openings can be accurately aligned. The shape of the posterior opening can be smaller then the anterior capsulotomy. The shape of the openings can be matched with a shape of a perimeter of the IOL or, more exactly stated, a perimeter about the optical structure of the IOL. Thus, the IOL can fit in the opening perfectly. Finally, the openings can be matched perfectly with an optical axis of the eye. Furthermore, if an optical axis of the IOL is aligned in a predetermined position within the circumference of the IOL, the optical structure of the IOL can be positioned in an optimal manner in the eye. Thus, the optics of the optical structure can be aligned in a predefined manner in the eye. For instance, optical axes may be aligned, but also other predefined configuration may be possible, for instance taking into account the quality of parts of the retina.

The support surfaces can be bounded areas on the anterior respectively the posterior supports that engage the capsular bag surface. In an embodiment, at least one anterior support comprises a posterior side that substantially completely engages the anterior surface of the anterior capsular bag part. In an embodiment, at least one posterior support comprises an anterior side that substantially completely engages the posterior surface of the anterior capsular bag part.

In an embodiment, the IOL comprises an indentation in said perimeter, providing an axially extending groove in the peripheral surface of said perimeter.

The indentation provides an axial fluid channel. The indentation is substantially axial. The indentation allows fluid communication through the eye.

The invention further pertains to an intra ocular lens structure (IOL) for placement in a capsular bag and securing the IOL in an opening in an anterior part of the capsular bag, with an anterior capsular bag flap at least partly surrounding said opening, said IOL having an anterior side which in use when the IOL is implanted in an eye is directed towards a cornea of the eye, and a posterior side which in use when the IOL is implanted in an eye is directed towards a retina of the eye, said IOL comprising:
  an optical structure;
  at least two posterior supports for when the IOL is implanted in the capsular bag residing in the capsular bag and extending away from said optical structure, said posterior supports adapted for in use providing support surfaces for engaging a posterior surface of an anterior capsular bag flap, and
  at least two anterior supports for when the IOL is implanted in the capsular bag residing outside the capsular bag and extending away from said optical structure, said anterior supports adapted for in use providing support surfaces for engaging an anterior surface of an anterior capsular bag flap,
wherein a posterior plane defined by the support surfaces of the posterior supports and an anterior plane defined by the support surfaces of the anterior supports are adapted for in use being spaced apart at a distance adapted for holding an anterior capsular bag flap between them for securing the IOL in said opening.

The invention further pertains to an intra ocular lens structure (IOL) for placement in a capsular bag and securing the IOL in an opening in an anterior part of the capsular bag, with an anterior capsular bag flap surrounding said opening, said IOL having an anterior side which in use when the IOL is implanted in an eye is directed towards a cornea of the eye, and a posterior side which in use when the IOL is implanted in an eye is directed towards a retina of the eye, said IOL comprising:
  an optical structure;
  at least two posterior supports for when the IOL is implanted in the capsular bag residing in the capsular bag and extending away from said optical structure, said posterior supports adapted for in use providing support surfaces for engaging a posterior surface of an anterior capsular bag flap, and
  at least two anterior supports for when the IOL is implanted in the capsular bag residing outside the capsular bag and extending away from said optical structure, said anterior supports adapted for in use providing support surfaces for engaging an anterior surface of an anterior capsular bag flap,
wherein said IOL comprises an indentation in said perimeter, providing an axially (A) extending groove in the peripheral surface of said perimeter. The axially extending groove provides a fluid channel allowing eye fluid to pass.

In an embodiment, the IOL is formed as one part. In an embodiment, the IOL is made from a polymer material. In an embodiment, the IOL is foldable. The polymer material allows the IOL to be rolled into a roll with a diameter smaller than 2.5 mm. In order to allow clamping of the anterior capsular bag part, at least the anterior supports are resilient, allowing the IOL to be inserted in the capsular bag and subsequently bringing the anterior supports through the opening in the anterior capsular bag part and in engagement with the anterior surface thereof. In fact, this allows holding the IOL in place.

In an embodiment, the at least two posterior supports extending away from said optical structure are in a functionally opposite direction with respect to one another. In an embodiment, the at least two anterior supports extending away from said optical structure in a functionally opposite direction with respect to one another.

In an embodiment, the anterior plane and said posterior plane are, in particular in use when clamping the capsular bag, spaced apart 5-100 micron. In particular, said posterior and anterior planes are spaced apart 5-70 micron, more specifically 5-50 micron.

In case the support surfaces run about parallel, this distance allows a clamping of the anterior capsular bag flap.

The posterior supports, or at least their support surfaces, may be angled towards the anterior side of the IOL. In that way, after implantation in the capsular bag, the posterior supports can urge against the posterior surface of the capsular bag flap. The posterior supports can be at an angle of up to 10°.

Alternatively or in combination, the anterior supports, or at least their support surfaces, may be angled towards the posterior side of the IOL. In that way, after implantation in the capsular bag, the anterior supports can urge against the anterior surface of the capsular bag flap. The anterior supports can be at an angle of up to 10°.

The posterior supports and the anterior supports, in summary, thus provide support surfaces that are positioned, in particular that are spaced apart at a distance, adapted for holding an anterior capsular bag flap between them. Before the IOL is inserted, in particular positioned in the capsular bag, one or more of the anterior support surfaces in axial sense may thus even be located posterior to one or more of the posterior support surfaces. Once the IOL is implanted and positioned, the support surfaces will hold the anterior capsular bag flap between them.

In an embodiment, the posterior supports and the anterior supports are in perimetrical sense or azimuthal direction shifted with respect to one another. This allows an easier manufacturing, in particular using for instance tooling or moulding technology. Furthermore, it provides easier placement and fixation in the capsular bag opening.

In an embodiment, the posterior supports and said anterior supports extend in perimetrical direction or in azimuthal direction about the optical structure. Thus, a good support of the capsular bag flap can be provided, and even a fixation of the IOL.

In an embodiment, the posterior supports and the anterior supports do not overlap. In fact, when viewed from the anterior side, if the anterior and posterior supports do not overlap, tooling can be simplified. Furthermore, it may even be possible to allow a smaller distance between the anterior and posterior planes. In fact, the support surface of the anterior support may be shifted to −100 micron past the support surface of the posterior support. In an embodiment, the shift may be −70 microns. In particular when the posterior support and the anterior support are resilient, the posterior support and the anterior support may clamp the capsular bag flap between them, thus fixing the IOL in the opening. Thus, when the supports do not overlap, the distance between the anterior and posterior plane can be between −100 and 100 micron. In an embodiment, the distance can be −70 to 100 microns. In particular, the distance can be between −70 micron and 70 micron. The negative values indicate that when not in use, the anterior support may be placed further in posterior direction, past the posterior support. In use however, when holding the capsular bag, the anterior support will be at the anterior side of the anterior part of the capsular bag, and the posterior support will be at the posterior side of the anterior part of the capsular bag.

In an embodiment, the IOL comprises a perimetrical surface surrounding said optical structure and said posterior support and said anterior support extending from said perimetrical surface. In particular, said perimetrical surface defines a radial surface for when implanted engaging a perimetrical edge of the anterior capsular bag flap which defines the perimeter of the opening.

This can provide alignment of the IOL. For instance, if the opening is non-circular, for instance elliptic, and the perimeter of the IOL matches the shape of the opening, the azimuthal orientation of the IOL can be fixed. Thus, specific optical structures can be aligned.

In an embodiment, at least one selected from said posterior supports and said anterior supports is a haptic. In particular, the haptic has an outer diameter of 8-12 mm.

It was found that the IOL thus fits in the capsular bag. It may function as a fail-safe if aligning with the opening fails.

In an embodiment, the IOL is formed in one piece, its thickness and flexibility adapted for insertion of the IOL into the eye in a folded manner via a micro insertion.

In an embodiment, the IOL further comprises an at least partially peripheral groove posterior to the posterior supports. In particular, said posterior groove opens in radial direction for receiving, when said IOL is implanted in an eye, at least an edge of a posterior capsular bag flap surrounding a posterior opening in a posterior part of the capsular bag. In an embodiment, the posterior groove is between 0.1 and 0.3 mm deep. In particular said posterior groove is between 0.05-0.2 mm wide. More in particular, the posterior groove is tapered.

The invention further pertains to a method for fixing the intra ocular structure (IOL) described above into an eye, where the IOL has a perimeter about an optical structure, the method comprising:

forming an opening within the anterior part of a capsular bag of an eye, the opening having a profile matching the perimeter of the IOL, said opening surrounded by an anterior capsular bag flap remaining after forming said opening;

inserting the IOL in the eye with the posterior supports extending in said capsular bag, and taking the anterior supports out the capsular bag with the anterior support surfaces resting on the anterior surface of the remaining anterior part of the capsular bag surrounding said opening and while leaving the posterior supports inside the capsular bag, the remaining part of the anterior part of the capsular bag surrounding the opening positioned between the posterior and anterior supports, thereby securing the IOL in the opening of anterior part of the capsular bag. The forming the opening may also be done at a separate action. The method thus relates to placement of the IOL only.

In an embodiment of the method, the opening is aligned with an axis of the eye and/or with the optical structure of the IOL. In case the optical structure is a lens, often an optical axis of this lens is aligned.

In an embodiment of the method, the opening is aligned with an axis and/or an azimuthal axis of the eye and an optical and/or azimuthal axis of the optical structure of the IOL.

In an embodiment of the method, the opening is circular with a centre aligned with an axis of the eye, and/or the optical structure comprises an optical axis that is aligned with the perimeter of the IOL.

In an embodiment of the method, the perimeter is circular.

In an embodiment of the method, the capsular bag further comprises a posterior part, said method further comprises:

forming a posterior opening in the posterior part of the capsular bag, said posterior opening surrounded by an posterior capsular bag flap remaining after forming said posterior opening;

urging the IOL when secured in the opening in the anterior part of the capsular bag in posterior direction in a direction of a retina of the eye, until an inner perimeter of the posterior capsular bag flap that defines the posterior opening surrounds a posterior groove in the IOL and which at least partially surrounds the optical structure posterior of the posterior supports, thereby securing. Thus the posterior capsular bag flap is secured to the IOL, posterior to the posterior supports.

In an embodiment, the IOL comprises an indentation in said perimeter, providing an axially extending groove in the peripheral surface of said perimeter.

In an embodiment, this indentation is provided between a posterior support and an anterior support. When positioned in the opening of the capsular bag, as explained the peripheral edge of the capsular bag will rest around the perimeter of the IOL. The indentation will then provide a passage for fluid.

The term "substantially" herein, such as in "substantially opposite" or in "substantially consists", will be understood by the person skilled in the art. The term "substantially" may also include embodiments with "entirely", "completely", "all", etc. Hence, in embodiments the adverb "substantially" may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

The term "functionally" herein, such as in "functionally opposite", will be understood by the person skilled in the art. It includes for instance exactly opposite, but deviations from exact positioning are also included, as long as in operation, the feature functionally behaves or has the effect of being for instance substantially opposite. The term "functionally" may therefore also include embodiments with "entirely", "completely", "all", etc. Hence, in embodiments the adverb "functionally" may also be removed. Where applicable, the term "functionally" may also relate to 90% or higher, such as 95% or higher, especially 99% or higher, even more especially 99.5% or higher, including 100%.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices or apparatus herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements.

The mere fact that certain measures are recited in mutually different dependent claims does not indicate that a combination of these measures cannot be used to advantage. In fact, many of the features of the current IOL can be combined to further improve easy implantation, or fixation.

The invention further applies to an apparatus or device comprising one or more of the characterising features described in the description and/or shown in the attached drawings. The invention further pertains to a method or process comprising one or more of the characterising features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 1 schematically depicts an embodiment of an IOL in anterior view;

FIG. 2 shows the embodiment of FIG. 1 in side view;

FIG. 3 shows a detail of FIG. 2 as indicated;

FIG. 10 shows a detail of FIG. 9 as indicated with the IOL of FIG. 1;

FIGS. 13 and 14 an alternative embodiment of the IOL of FIG. 8, in front view and in perspective partly from the rear;

The drawings are not necessarily on scale.

DESCRIPTION OF PREFERRED EMBODIMENTS

In this description, first relevant parts of the eye will be described in FIGS. 19A, 19B and 19C. In FIGS. 1-11, some particular embodiments of an intraocular lens structure (IOL) and its position in an eye (FIGS. 9-11) will be described, and a procedure for placing such an IOL in an eye.

The Eye

Figures 19A, 19B:
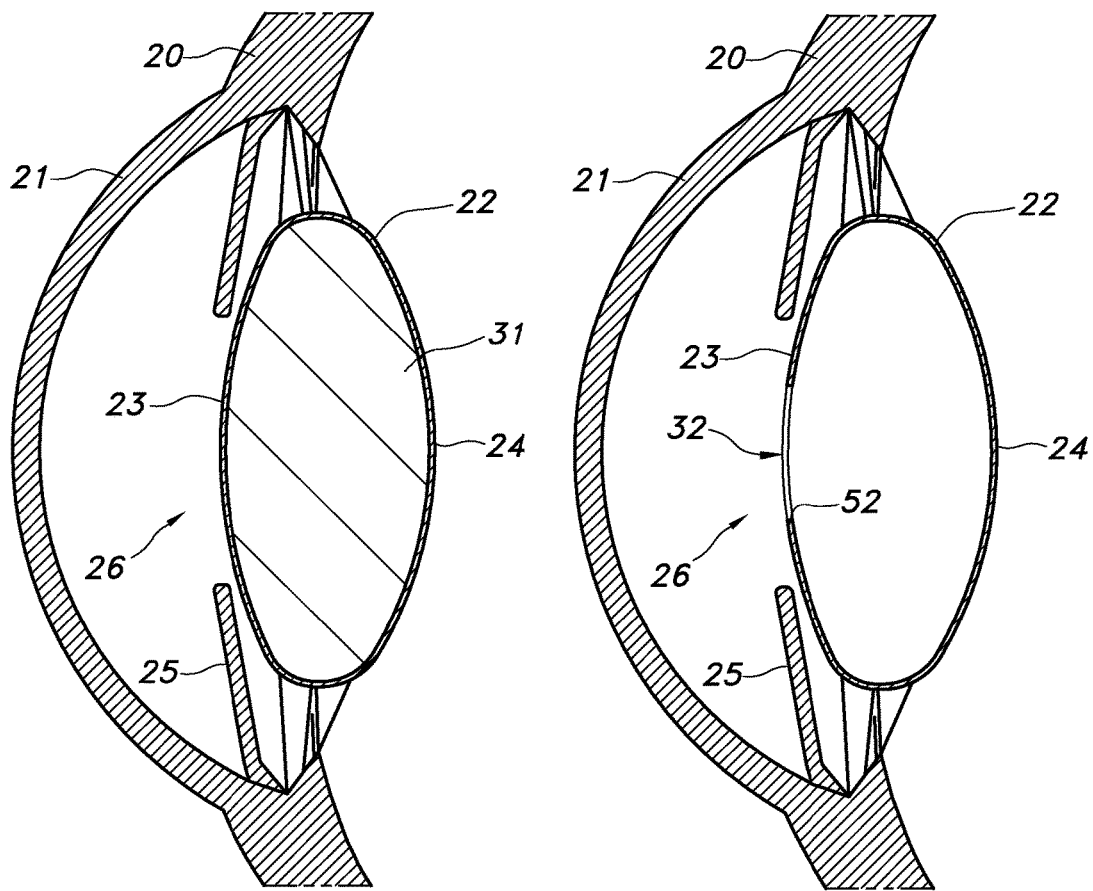
FIGS. 19A and 19B schematically indicate a cross section through an eye before and after removal of the natural lens, and FIG. 19C a front view of FIG. 19B.

In FIGS. 19A and 19B, schematically a cross section through an eyeball 20 is depicted. In FIG. 19A, the eyeball 20 has a cornea 21, iris 25, pupil 26, and capsular bag 22 with a natural lens 31. The capsular bag 22 has an anterior part 23 and a posterior part 24. In FIG. 19B, the eyeball 20 is shown after the natural lens 31 has been removed, leaving the empty capsular bag 22 with an opening 32, usually having a circular or an elliptic shape. The opening 32 is in the anterior part 23 of the capsular bag 22. In many cases, the centre of the opening 32 will be on an axis of the eye. The axis are defined in FIG. 12.

Figure 19C:
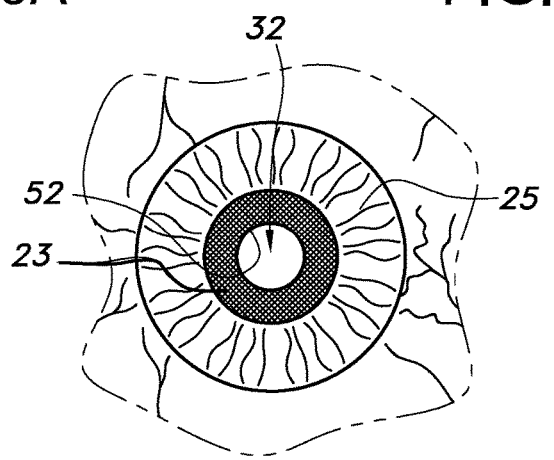

FIG. 19C shows part of the eyeball in front view, showing the iris 25, the anterior part 23 of the capsular bag with opening 32 and the edge of the opening 52. This edge 52 is also referred to as the 'perimetrical edge' 52.

In some patients, the posterior part 24 of the capsular bag 22 may not be clear anymore. In these cases or to generally avoid post surgery posterior capsular opacification, additionally an opening in the posterior part 24 or the capsular bag 22 may be made, referred to as the posterior opening, or the posterior part 24 of the capsular bag may be removed.

In the previous paragraph, the adjectives 'anterior' and 'posterior' are used. As explained before, the terms "anterior" and "posterior" relate to an arrangement of features relative to the propagation of the light into the eye. Thus, light enters cornea and iris, which are anterior parts of the eye, and propagates to the retina that is located in the posterior part of the eye. Thus, for instance the capsular bag 22 has an anterior part 23 and a posterior part 24. The anterior part, in turn, has a surface directed towards the cornea 21 and the iris 25. This surface will be referred to as the anterior surface of the anterior part 23 of the capsular bag 22. The opposite surface, at the inside of the capsular bag 22, will thus be referred to as the posterior surface of the anterior part 23 of the capsular bag 22.

The Intraocular Lens Structure (IOL)

Next, some embodiments of the intraocular lens structure (IOL) will be described. FIG. 1 schematically depicts an embodiment of an intra ocular lens structure (IOL) 1 in anterior view. The anterior side is the side of the IOL 1 that is directed towards the cornea 21 when said IOL 1 is placed in an eye. The side of the IOL 1 that is directed towards the retina after the IOL is implanted in an eye is here referred to as the posterior side of the IOL 1. When a natural lens 31 has to be removed from an eye, usually an opening 32 is made in the anterior part 23 of the capsular bag 22. Subsequently, the natural lens 31 is removed. In specific cases, such as pediatric patients, there may also be a posterior opening made in the posterior part 24 of the capsular bag 22, the part of the capsular bag 22 that is positioned between the natural lens 31 and the retina. The opening 32 and the posterior opening are usually aligned. The openings are often circular, but other shapes may be possible, certainly when using laser-assisted capsulotomy. The openings are usually aligned with an optical axis of the eye, but other positions maybe used. Around the openings, a ring of capsular bag tissue or membrane remains. This ring is also referred to as a capsular bag flap. The ring or flap has an edge 52 bounding the perimeter of the opening 32, or in fact defining the opening 32. The opening 32 has a radial direction, running from the centre of the opening 32 outwards to its perimeter 52.

The IOL 1 comprises an optical structure 2. The optical structure 2 in many cases is a lens, in fact an anterior lens and a posterior lens. In embodiments like the one shown in FIG. 1, the optical structure 2 has an anterior lens structure surface 3 and a posterior lens structure surface 4, see FIG. 2. The optical structure can further be provided with any type of optical structure known in IOLs. In this description, the nature of the optical structure should further not be considered limited. The optical structure can comprise a lens or a closure cap. In an embodiment, both the anterior and posterior sides are provided with a curved surface to provide one or more lenses. Examples of lens optics are a mono focal lens, an astigmatic lens, a multifocal lens, an accommodative lens or a sector bifocal lens such as for instance disclosed in PCT/NL2012/050115, which is incorporated by reference as if fully set forth. The optics may be refractive, diffractive, or a combination of both. Furthermore or in combination, the optical structure may comprise an optical filter, and/or a functional layer known to a skilled person. The optical structure may comprise active and/or passive elements. An example of an active element is for instance an liquid crystal optics.

An IOL 1 usually is substantially a flat structure. Its thickness is about 0.1-1 mm. The diameter of IOL 1 usually is about 7-12 mm. The optical structure usually has a diameter of between 4-7 mm. In most embodiments, the optical structure has a diameter of 5-7 mm. The optical structure often is biconvex.

In such a mainly flat structure, an axial sense Ax can be distinguished which can have a posterior direction and an anterior direction. Furthermore, a radial sense Ra can be distinguished. Finally, an azimuthal sense Az can be distinguished, which can have a clockwise and counter clockwise direction. In case the optical structure is a simple, mono focal lens, the axial sense is the optical axis, and the radial sense is the radial direction of the lens. In FIGS. 1 and 2 these are indicated. In case of other optical structures, the axial, radial and azimuthal sense will be clear to a skilled person.

In an embodiment, the IOL 1 is made from a polymer material. In particular, the IOL 1 is from a polymer material that is foldable. In particular, the supports are resilient. The IOL 1 in an embodiment is made in one piece. In particular, The IOL 1 is pliable to allow it to be rolled up in a small roll with a diameter smaller than 2.5 mm. In particular, it allows rolling the IOL up to a diameter smaller than 1.8 mm. On the other hand, the IOL is dimensionally stable, in particular flexible to be able to unfold from its rolled-up state and to return to its original shape once it is inserted in the capsular bag.

Figure 4:
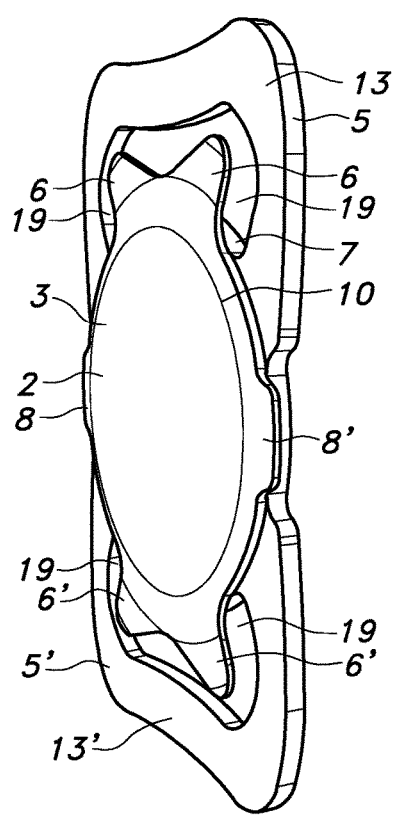
FIG. 4 shows the embodiment of FIG. 1 in perspective view showing the anterior side.

The embodiment of FIG. 1 is further also shown in detail in FIGS. 2-4, in which FIG. 2 shows the embodiment of FIG. 1 in side view, FIG. 3 shows a detail of FIG. 2 as indicated in FIG. 2, and FIG. 4 shows the embodiment of FIG. 1 in perspective view, from the anterior side.

The IOL comprises a perimeter 7 about the optical structure 2. The perimeter 7 has a perimetrical surface. The perimeter 7 can match the shape of the opening in the capsular bag. If for instance the opening is circular, the perimeter can be circular. The size of the perimeter is such that it may be a little oversized to stretch the size of the capsular opening a little or matches the size of the opening. In the embodiment of FIG. 1, the optical structure 2 comprises a curved surface providing a lens. The lens in this embodiment is circular and has an optical axis. The perimetrical surface here extends parallel to the optical axis. The perimeter provides here a cylindrical surface. In case of a circular perimeter 7, the perimetrical surface is circle cylindrical, in the embodiment of FIG. 1 even right circle cylindrical. A non-circular shape of the opening and the perimeter 7 can have advantages for preventing rotation of the IOL 1 about the optical axis. For instance, the opening can be elliptical, and the perimeter 7 can be elliptical, matching the elliptical shape of the opening. Alternatively, an alignment feature, for instance a cam, can be provided at the perimeter 7, and a matching feature can be provided to the opening. The rotational fixation can for instance be advantageous in case of astigmatic optics. In an embodiment, for instance shown in FIG. 1 and FIG. 8, the diameter of perimeter 7 is larger than the perimeter 10 of the optical structure 2. Perimeter 7 can for instance be 0.5-2 mm larger than perimeter 10 of the optical structure 2.

The IOL 1 comprises posterior supports 5, 5' here at opposite sides of the optical structure 2. The posterior supports 5, 5' extend away from the optical structure. In particular, the posterior supports 5, 5' extend away in sideward direction with respect to the optical structure 2. The posterior supports 5, 5' have support surfaces 13, 13', also referred to as the support surfaces of the posterior supports 5, 5'. These support surfaces 13, 13' are here in a plane, referred to as the posterior plane. In the specific embodiment of FIG. 1, where the perimeter discussed above is cylindrical, the posterior plane is perpendicular to the cylindrical surface of the perimeter 7.

The posterior supports 5, 5' here form loops that have two ends attached to the perimeter 7.

The optical structure 2 usually has a diameter of between 4-7 mm. The perimeter 7 usually has a diameter of between 4-7 mm. In the embodiments shown in the drawings, the anterior supports 6, 6' and the posterior supports 5, 5' are attached to the perimeter 7.

When the IOL 1 is implanted, the support surfaces 13, 13' of the posterior supports 5, 5' engage the posterior surface of the anterior part 23 of the capsular bag 22. In an embodiment, the posterior supports 5, 5' and thus at least part of the support surfaces can be angulated between 0-10 degrees in anterior direction. In an embodiment, when implanted, the surface of perimeter 7 engages or almost engages the edge 52 of the opening in the anterior capsular bag, and the support surface 13, 13' of the posterior supports 5, 5' in fact nestles against the posterior surface of the anterior capsular bag. To that end, the support surface 13, 13' can be adapted to hold the surface of the capsular bag. For instance, cams or rims may be provided.

At least one of the surfaces of the posterior supports can be roughened, for instance sand blasted, in order to prevent reflections of light.

The IOL 1 further comprises anterior supports 6, 6'. The anterior supports 6, 6' also extend sideward with respect to the optical structure 2. The anterior supports provide the support surfaces 14, 14' of the anterior supports 6, 6'. When the IOL 1 is implanted, these anterior supports 6, 6' are outside of the capsular bag 22. The support surfaces 14, 14' are designed and adapted for, when the IOL 1 is implanted, engaging the anterior surface of the anterior part of the capsular bag. Again, these support surfaces 14, 14' are in a plane, referred to as the anterior plane. In an embodiment, when implanted, the surface of perimeter 7 engages or almost engages the edge 52 of the opening in the anterior capsular bag, and the support surface 14, 14' of the anterior supports 5, 5' in fact can be made to nestle against the anterior surface of the anterior capsular bag. Both surfaces are thus in almost complete physical contact. To that end, the support surface 14, 14' can be adapted to hold the surface of the capsular bag. For the anterior supports to actually reach outside the capsular bag and be able to nestle against the anterior surface of the anterior capsular bag, usually requires some manipulation of the person implanting the IOL 1.

The anterior plane is functionally parallel to the posterior plane. Side view FIG. 2 shows this. In particular, these planes are parallel when holding the capsular bag 22 between them. The distance between the posterior support surfaces 14, 14' of the anterior support 6, 6' and the anterior support surfaces 13, 13' of the posterior support 5, 5' is such that they can hold the anterior part 23 of the capsular bag 22 between them. The anterior supports 6, 6' and the posterior supports 5, 5', are positioned such that their support surfaces comprise a spacing 11 between them. In fact, the distance between the posterior plane and/or the anterior plane is adapted for holding the anterior capsular bag flap 23 between them for securing the IOL 1 in the opening when the IOL 1 is implanted. In fact, the distance between the posterior plane and the anterior plane can be adapted to the thickness of the anterior part of the capsular bag. It was found that the posterior supports 5, 5' and the anterior supports 6, 6' were able to hold the anterior capsular bag flap between them if the distance is between 5 and 100 microns. In particular, the posterior plane and the anterior plane are spaced apart 15-50 microns. The distance provides the spacing 11. In case the distance is less than 20 microns, in particular less than 10 microns, the flap will be securely clamped and possible rotation of the lens prevented.

In the embodiment of FIG. 1, the posterior supports 5, 5' and the anterior supports 6, 6' are staggered. In fact, when viewed from the anterior direction, the posterior supports 5, 5' and the anterior supports 6, 6' do not overlap. This may also be referred to as that the posterior supports 5, 5' and the anterior supports 6, 6' are staggered in a perimetrical sense or azimuth sense (Az, FIG. 1). In this sense, staggered is used as in a 'staggered junction'.

In particular, when the posterior supports 5, 5' and the anterior supports 6, 6' are staggered, the posterior plane and the anterior plane are parallel or substantially parallel when the anterior part of the capsular bag is held between them.

In the embodiment of FIG. 1, the posterior supports 5, 5' of IOL 1 are closed loops. In the embodiment of FIG. 1, the posterior supports 5, 5' of IOL 1 have a diameter (in other words provide the IOL with a diameter) of about 8-12 mm, in particular 7-12 mm. The thickness of the posterior support can be between 0.15-0.4 mm. In particular, the thickness can be between 0.2-0.4 mm. More, the thickness can be in particular 0.20-0.35 mm. Specifically the thickness of the posterior supports may be between 0.25 and 0.35 mm.

Alternatively, the ends of the loops may also be removed, turning posterior supports 5, 5' in fact each into two posterior supports, resulting in four posterior supports 5, 5'. The radially extended posterior supports or loop supports may in fact act as safeguard if placement of IOL 1 in the opening 32 can not be accomplished for some reason.

The thickness of the anterior supports 6, 6' can be between 0.04 and 0.25 mm. In particular the thickness can be between 0.04 and 0.20 mm. More in particular, the thickness can be between 0.05 and 0.20 mm. Specifically, the thickness can be between 0.05 and 0.10 mm.

In the embodiment of FIG. 1, the IOL 1 at or near the perimeter 7 has at least one in perimeter or azimuthal direction extending space 19 between a posterior support 5, 5' and an anterior support 6, 6'. This space facilitates manufacturing, and also facilitates getting the anterior supports 6, 6' through the opening 32 and out of the capsular bag as it provides room for insertion of an instrument when inserting and positioning the IOL 1. In the embodiment of FIG. 1, at each transition from anterior supports 6, 6' to posterior supports 5, 5' there is a azimuthal space 19.

It was found that in order to support the posterior side of the anterior part of the capsular bag, the posterior supports 5, 5' extend at least about 0.5 mm away from the perimeter, in radial direction. In particular, the posterior supports 5, 5' extend at least 1.0 mm in radial direction.

It was found that in order to support the anterior side of the anterior part of the capsular bag, at least one of the anterior supports 6, 6' extend at least about 0.3 mm away from the perimeter, in radial direction. In particular, the anterior supports 6, 6' may extend at least 0.4 mm. More in particular, the anterior supports may extend at least 0.5 mm in radial direction.

In the embodiment of the IOL 1 of FIG. 1, the IOL 1 has additional anterior supports 8, 8'. These anterior supports are here referred to as anterior lips 8, 8'. These in use also extend outside the capsular bag 22. They complement the other anterior supports 6, 6' and provide additional clamping of the anterior capsular bag part 23. The anterior lips 8, 8' have posterior surfaces 17, 17' that rest against the outside of the capsular bag 22, against the anterior surface of the anterior capsular bag part 23. The anterior lips 8, 8' here extend in perimeter (or azimuthal) direction about 0.1-2 mm. The anterior lips 8, 8' extend in radial direction, i.e. away from the optical structure 2 and the perimeter 7, about 0.1-1.3 mm. In particular it is about 0.4-1.0 mm. Specifically, it is about 0.4-0.6 mm. In this embodiment, the anterior lips 8, 8' extend about 0.3 mm.

Figure 8:
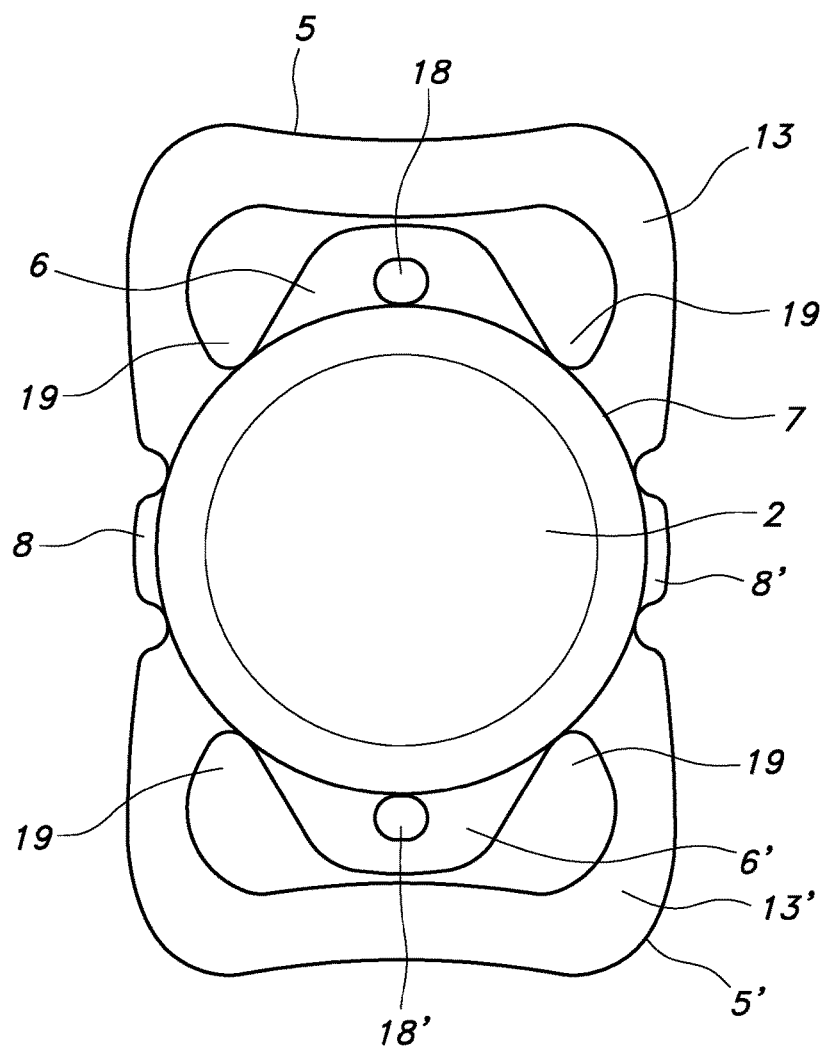
FIG. 8 shows yet another alternative embodiment of an IOL in anterior view.

In FIG. 8, an embodiment of an IOL 1 is shown in which the anterior supports 6, 6' have an alternative shape. In this embodiment, the anterior supports 6, 6' are provided with a support opening 18, 18'. Through these support openings 18, 18', an instrument can be inserted for pulling the anterior supports 6, 6' back through the opening 32 in the capsular bag after the IOL was inserted in the capsular bag. The anterior supports 6, 6' thus reach outside the capsular bag. The diameter of the support opening 18, 18' can be 0.2-1.5 mm. In particular, the diameter can be 0.2-1.0 mm.

Figure 6A:
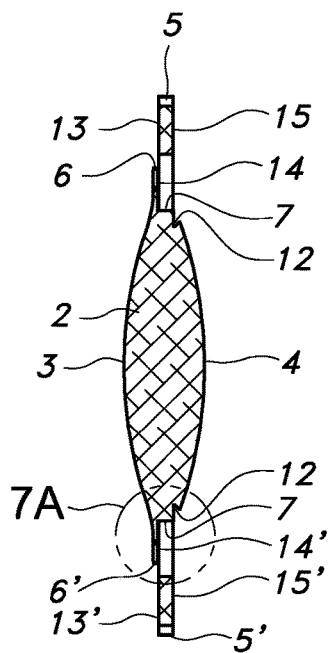
FIG. 6A shows a cross section of the IOL of FIG. 1 with the posterior feature of FIG. 1.
Figure 6B:
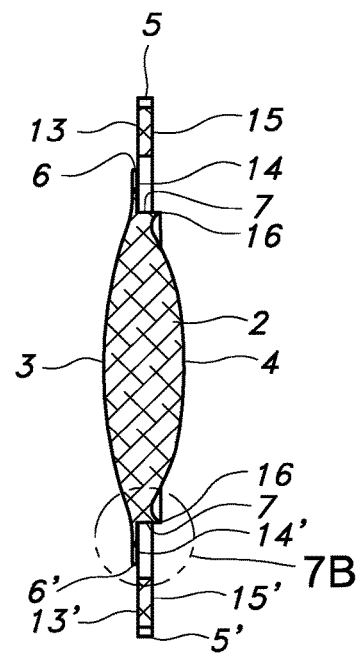
FIG. 6B shows a cross section of the IOL of FIG. 5 with the alternative posterior feature.

In FIGS. 6A and 6B, two different embodiments of posterior features that influence the posterior part of the capsular bag can be seen.

Figure 5:
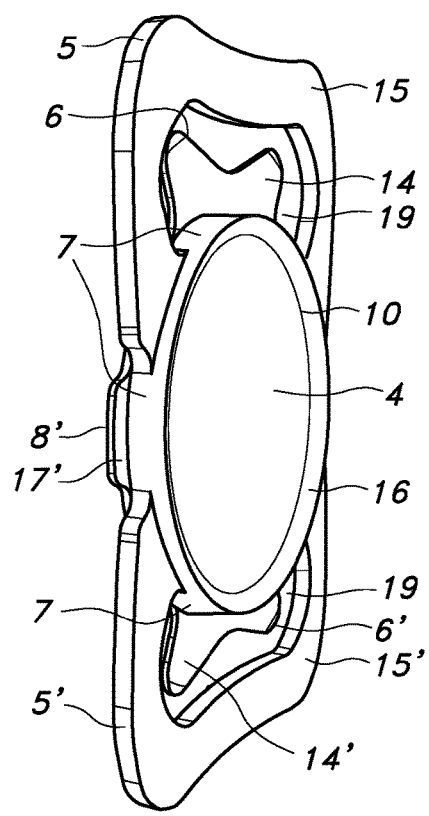
FIG. 5 schematically depicts a posterior side of the IOL of FIG. 1, with an alternative posterior feature.
Figure 7A:
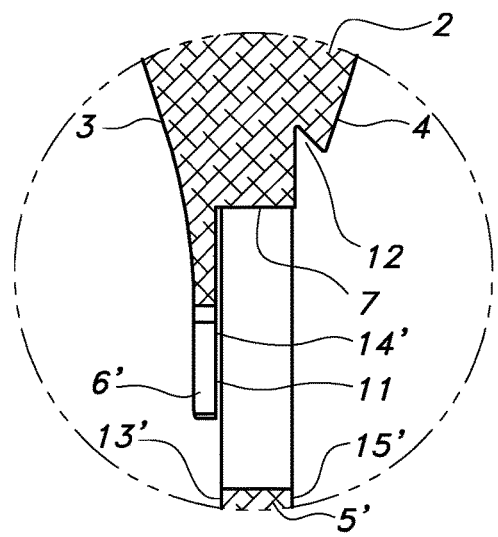
FIG. 7A shows a detail of FIG. 6A as indicated.
Figure 7B:
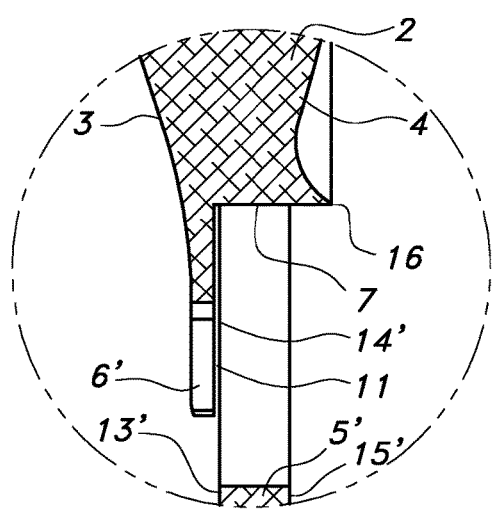
FIG. 7B shows a detail of FIG. 6B as indicated.

In FIGS. 5, 6B and 7B, showing respectively a perspective view from the posterior side, a cross section and a detail of the cross section of FIG. 6B as indicated, the posterior side of the IOL 1 at and near the perimeter is provided with a sharp rim 16 to prevent growth of tissue from the posterior capsular bag part. Such growth of tissue can cause posterior capsule opacification.

In FIGS. 2, 3, 6A and 7A, an alternative embodiment of posterior features is shown. FIG. 2 shows a side view, FIG. 3 shows a detail as indicated, FIG. 6A shows a cross sectional view of the IOL of FIG. 1, and FIG. 7A shows a detail as indicated in FIG. 6A.

The IOL of this embodiment has a circumferential posterior groove 12, extending posterior to the posterior supports 5, 5' and the anterior supports 6, 6'. In fact, the posterior groove 12 is here provided posterior to the posterior surface 15, 15' of the posterior supports 5, 5'. The posterior groove 12 is provided to receive and hold the edge around the posterior opening, i.e., the opening in the posterior capsular bag. As explained, such a posterior opening can be made by a second capsulotomy performed on the posterior part 24 of the capsular bag 22. The edge around the posterior opening is slipped into posterior groove 12 after the IOL 1 is positioned in the opening in the anterior capsular bag part. To that end, the IOL can be gently urged backward until the edge or rim of the posterior opening slips into the posterior groove 12. The posterior groove 12 here has a depth of 0.1-0.3 mm. The posterior groove 12 is shaped to receive the edge around a posterior opening. The posterior groove 12 can be a rectangular groove. Here it is wedge-shaped. It has walls at an angle of between 10 and 60 degrees, in particular about 30-60 degrees, specifically 40-50 degrees. This posterior groove 12 will seal the posterior opening, preventing capsule opacification and/or leakage of the vitreous.

The IOL Positioned in the Eye

Figure 9:
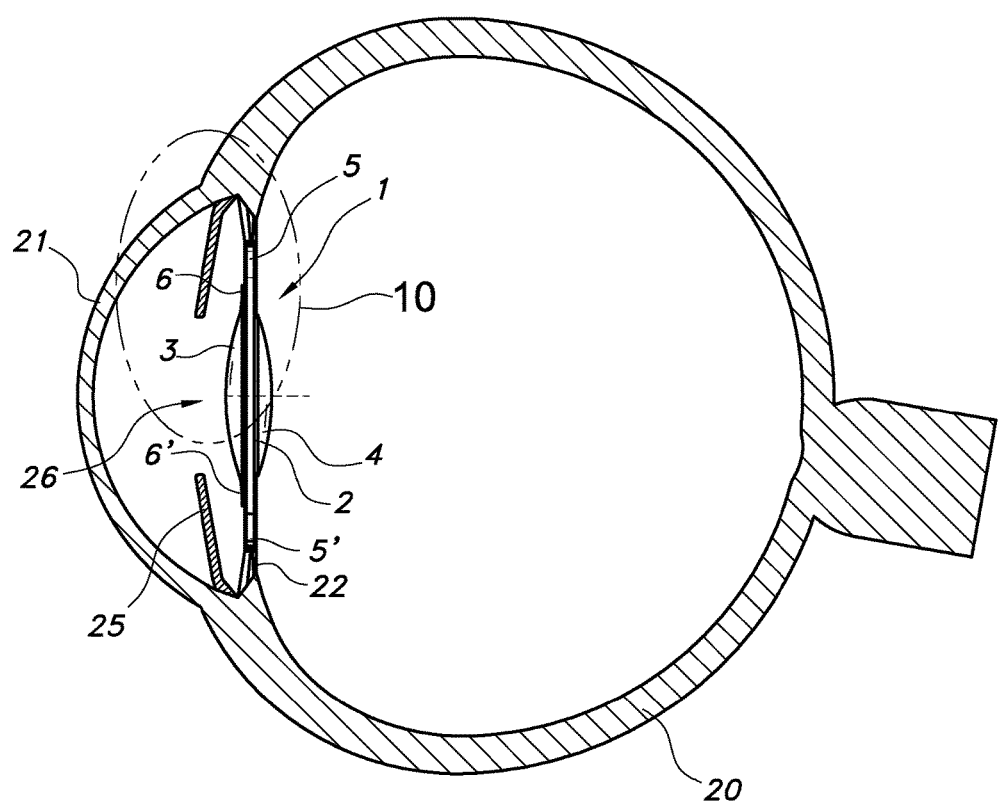
FIG. 9 shows an eyeball with an IOL.

FIG. 9 shows in cross sectional view an eyeball with an IOL 1 in inserted position inside capsular bag 22. The eyeball 20 has a cornea 21, an iris 25 with a pupil 26, and the capsular bag 22.

Figure 12:
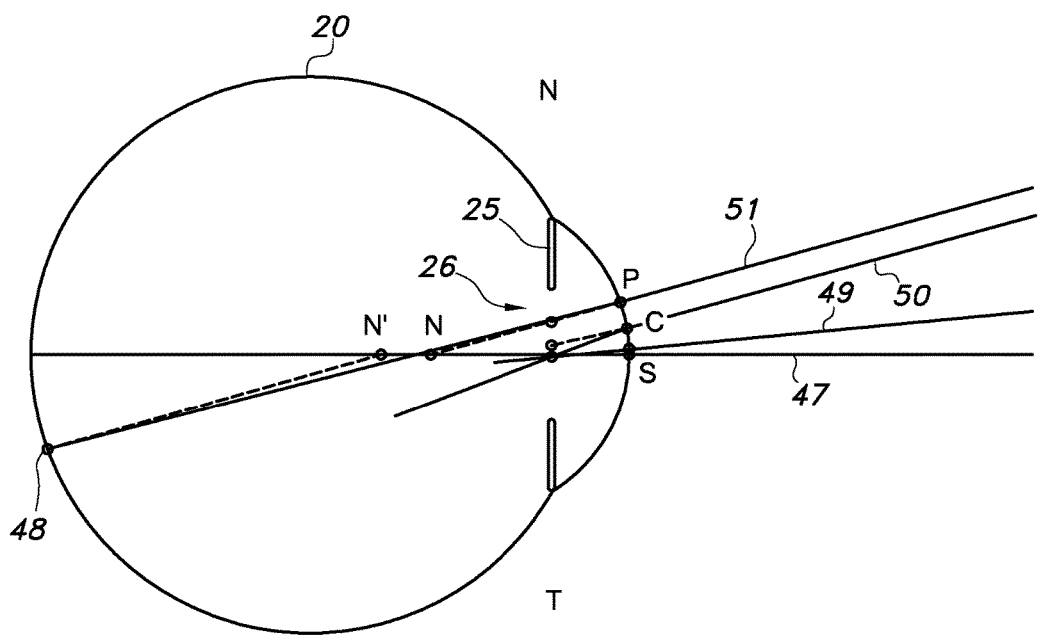
FIG. 12 an eye from above showing axes in the eye.

In FIG. 12, showing a cross section through the eye from above (N=Nasal side, T=Temporal side), several axes of the eye 20 are defined:

1. The visual axis 51, which goes through the fixed object point and the nodal point N of the eye. If the function of the nodal points is taken into account, the ray, which represents the visual axis 51, passes to the retina through the fovea 48.

2. The optical axis 47, which is perpendicular to the cornea surface and passes the iris 25 pupil 26 at the midpoint. Since the fovea 48 is not located central to the eyeball 20, the optical axis 47 differs from the visual axis 51. The optical axis 51 is the geometrical symmetry axis of the eye-ball system and is different from the optical central ray, which reaches the central point of the fovea and passes obliquely through the eye system.

3. The line of sight 50 is the axis, which goes through the object point and the centre of the entrance pupil 26. It is the ray, which passes through the centroid of the light bundle and is the axis of the ray cone, which enters the eye 20. Typically, the angle between the line of sight and the optical axis 47 lies in the range between 3° and 8°. The centre of the entrance pupil 26 is shifted towards the nasal side due to the asymmetrical imaging through the cornea system and the off-axis position of the fovea.

4. The pupillary axis 49, which passes through the centre of the entrance pupil 26 and is perpendicular to the front surface of the cornea.

The field of view for monocular sight covers the whole retina without the small portion of the blind spot. Usually humans tend to rotate the eye to the most favourable position where the image is generated in the fovea 48. If the eye 20 is moved in this way into a position of optimal orientation so that the image is in the central part of the fovea, the optical system of the eye is not used as a centered system. Nevertheless, the tilt is small and spherical aberration and astigmatism are the dominating aberrations of the eye.

In FIG. 10, a detail of FIG. 9 is shown with the IOL 1 of FIG. 1 inserted. The IOL 1 in this example is provided with the posterior groove 12 described earlier.

Here, the posterior capsular bag 24 has the posterior opening explained earlier. The rim of the posterior opening is positioned in the posterior groove 12. The anterior capsular bag flap (a ring of capsular bag membrane material) which remains after an opening is made in the anterior capsular bag part 23 is held between the anterior support 6 and the posterior support 5. The support surface of the anterior support 6 and the support surface of the posterior support 5 both rest against the anterior capsular bag flap, and in fact, although perhaps not indicated that way, may even clamp that flap between them.

Figure 11:
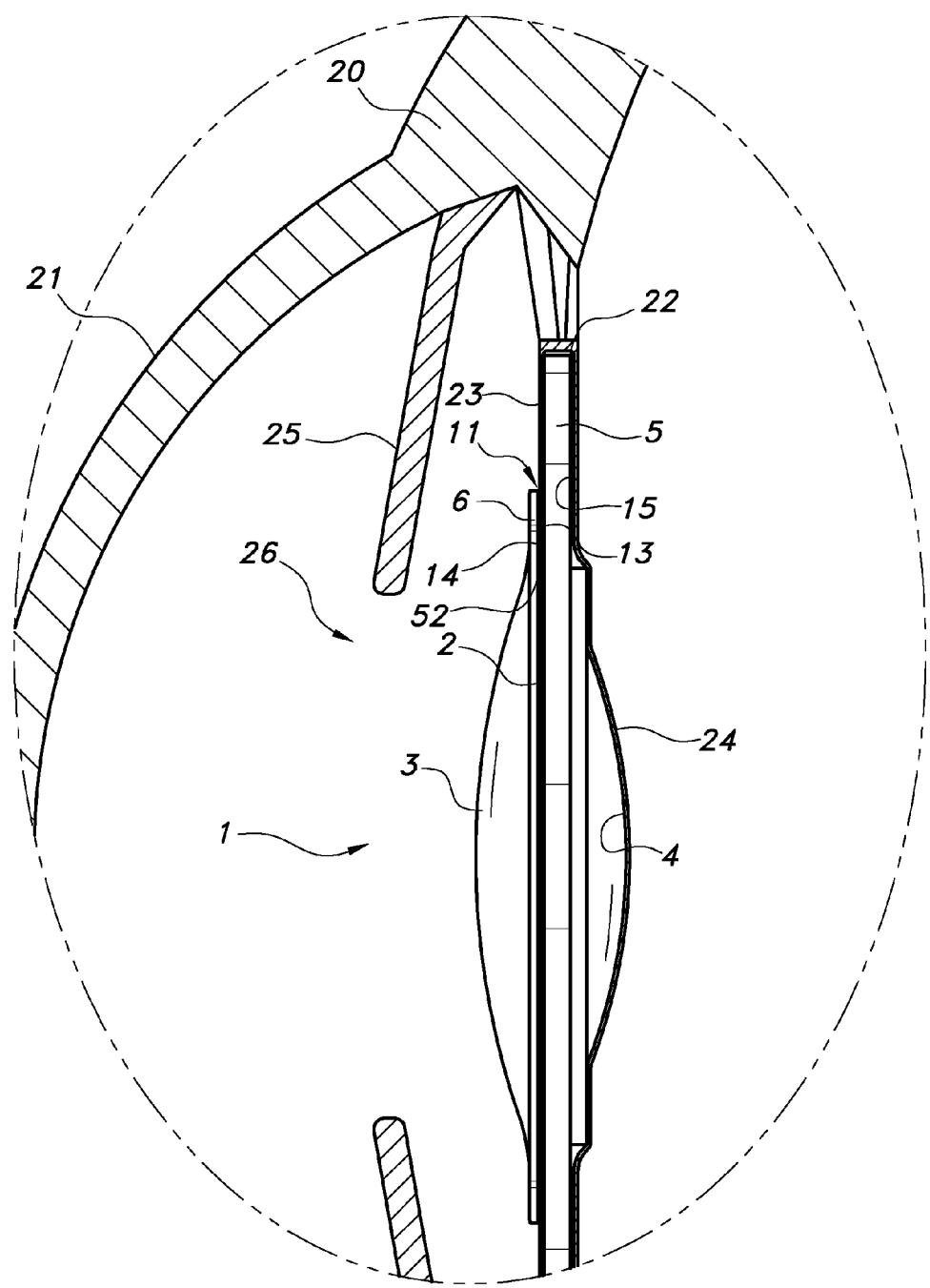
FIG. 11 shows a detail of FIG. 9 as indicated, but with an IOL with an alternative posterior feature and a posterior capsular bag part that is intact.
Figure 11:
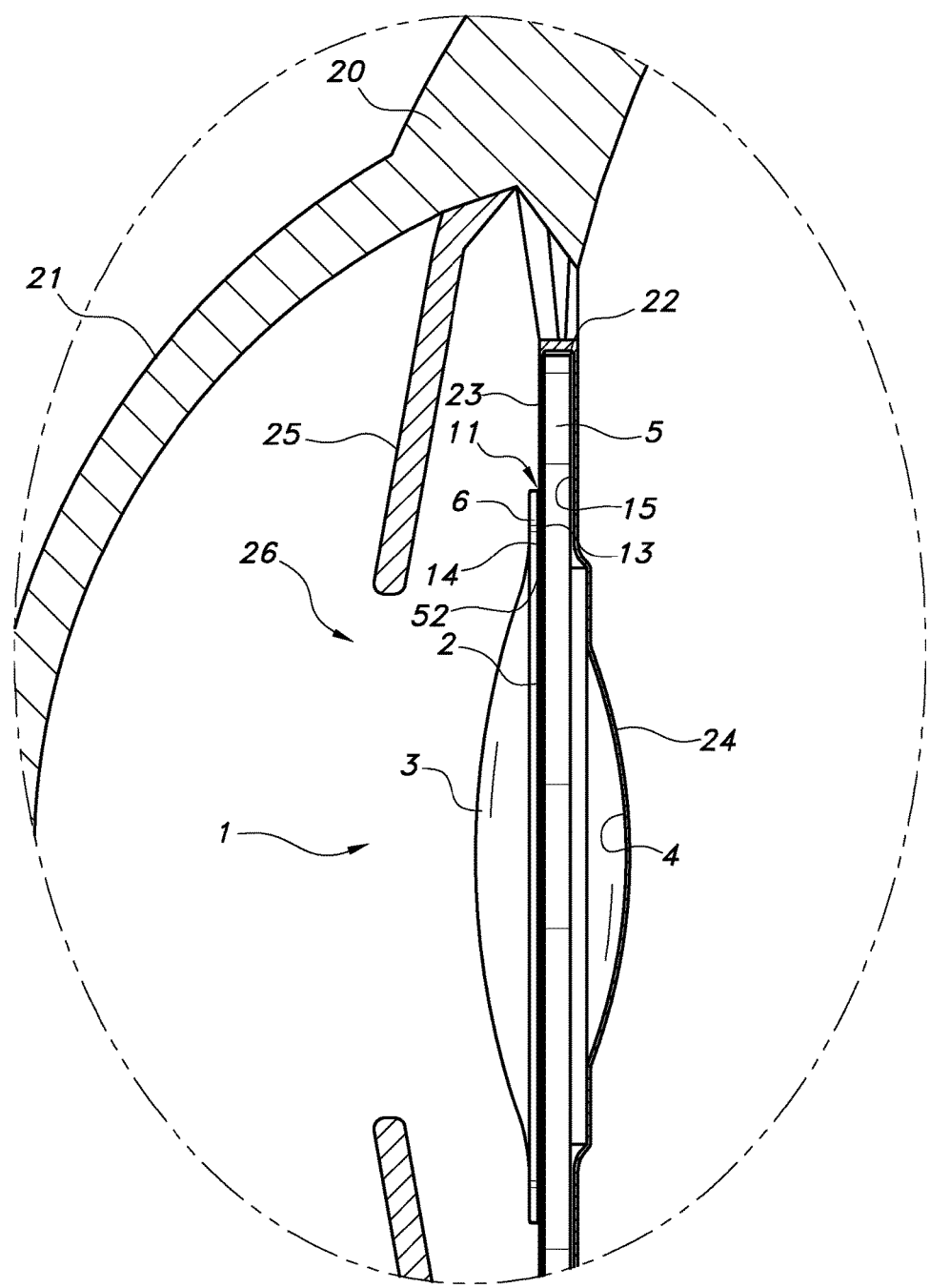

In FIG. 11, a detail similar to that of FIG. 9 is shown, but with an IOL 1 with an alternative posterior feature. In this case, the posterior capsular bag part 24 does not have an opening: the posterior capsular bag part 24 is intact and rests against the posterior surface 4 of IOL 1.

In both FIGS. 10 and 11, the posterior supports 5, 5' have a large diameter. The IOL 1, however, is positioned in opening 32 by means of the anterior and posterior supports, possibly combined with mutual fitting of perimeter 7 and the length of the perimeter of opening 32. Thus, the radial dimension of the posterior supports 5, 5' may be reduced.

Insertion of the IOL in an Eye

Insertion of the IOL 1 described so far will be explained below. An example of a procedure of making the incision and implanting the IOL is as such for instance described in U.S. Pat. No. 5,376,115, which is incorporated by reference as if fully set forth. In particular, it describes:

A surgical method gaining in popularity is the phacoemulsification technique, that utilises ultrasonic vibrations to fragment the lens nucleus, thus allowing removal of the lens material through an incision that is approximately 3 mm long. The benefits of a small incision are faster visual rehabilitation, faster healing and less astigmatism than with conventional large incisions. A hollow titanium needle with a diameter of about 1 mm is activated to vibrate by a magnetostrictive ultrasonic mechanism. The mechanical vibrations transform the lens into an emulsion, hence the name phacoemulsification.

As the phacoemulsification technique has been refined the construction of the incision has developed to allow sealing of the wound without the need for sutures—"self sealing incisions".

According to the reference, the technique is described for instance in J Cataract Refract Surg 16(5) (1990) pp. 567-577 by Menapace, R. et al and in Ophthalmology (U.S.) 100(2) (1993) pp. 159-163 by Ormerod, L. D. et al.

U.S. Pat. No. 5,376,115 further describes an example of insertion of an IOL.

This may be combined with the following procedure. Before inserting the IOL 1 into the capsular bag, first an opening is made in the anterior part of the capsular bag. Using for instance a laser device like the Femto laser, an opening or aperture can be made in the anterior membrane or anterior capsule of the capsular bag that has a precise shape and precise position. This procedure is also referred to as 'Capsularhexis', although recent literature refers to a laser-based procedure as 'Capsulotomy', and uses that term in contrast to 'Capsularhexis', which term is then used to refer to mechanically tearing or cutting an opening in the capsular bag. Other laser-based procedures are currently also developing. In these procedures, a laser beam is directed through the cornea and into the eye, where its energy is absorbed in an internal structure in order to cut that structure. In one of these procedures, the anterior capsular bag membrane is coloured with a light-absorbing agent. The absorption properties of that light-absorbing agent are selected in order to absorb the laser beam energy.

In many cases, for instance in case of a cataract, in a next step the cloudy natural lens is removed through the opening in the capsular bag. In this step, the natural lens can be treated with a laser first, before it is removed, for instance with a phaco emulsification device. Removal of the natural lens as such is known to skilled person.

In an optional next step, a posterior opening can be made in the posterior part of the capsular bag, in the posterior membrane or posterior capsule of the capsular bag.

An example of such a classic Capsularhexis procedure and the use of a laser device in such a procedure is described in U.S. Pat. No. 8,409,182, which is incorporated herein by reference as if fully set forth. For instance in column 3, an example of steps in a Capsularhexis procedure or, more specific, a capsulotomy procedure, is described. The laser-assisted procedure allows accurate positioning as well as shaping of the opening. Furthermore, such a procedure can leave a relatively strong edge 52 around the created opening in the capsular bag. In particular, regarding a laser-based procedure the following was found.

METHODS: Capsulotomies performed by an optical coherence tomography-guided femtosecond laser were evaluated in porcine and human cadaver eyes. Subsequently, the procedure was performed in 39 patients as part of a prospective randomized study of femtosecond laser-assisted cataract surgery. The accuracy of the capsulotomy size, shape, and centration were quantified and capsulotomy strength was assessed in the porcine eyes.

RESULTS: Laser-created capsulotomies were significantly more precise in size and shape than manually created capsulorhexes. In the patient eyes, the deviation from the intended diameter of the resected capsule disk was 29 μm±26 (SD) for the laser technique and 337±258 μm for the manual technique. The mean deviation from circularity was 6% and 20%, respectively. The centre of the laser capsulotomies was within 77±47 μm of the intended position. All capsulotomies were complete, with no radial nicks or tears. The strength of laser capsulotomies (porcine subgroup) decreased with increasing pulse energy: 152±21 mN for 3 mJ, 121±16 mN for 6 mJ, and 113±23 mN for 10 mJ. The strength of the manual capsulorhexes was 65±21 mN.

CONCLUSION: The femtosecond laser produced capsulotomies that were more precise, accurate, reproducible, and stronger than those created with the conventional manual technique.

Source: J. Cataract Refract. Surg. 2011; 37:1189-1198 Q 2011 ASCRS and ESCRS.

Test further showed the following results.

METHODS: Ten fresh pig eyes were randomly assigned to femtosecond laser-assisted capsulotomy or manual capsulotomy. The capsule was immersed in hyaluronic acid, and retractors were fixed in the capsule opening with a pull-force measuring device. The force necessary to break the capsulotomy was measured in millinewtons (mN); the maximum stretching ratio was also assessed.

RESULTS: The observed mean rupture force (i.e., maximum amount of force measured immediately before tissue rupture) was 113 mN±12 (SD) in the laser-assisted procedure and 73±22 mN in the manual procedure (P<0.05). The stretching ratios were 1.60±0.10 (femtosecond) and 1.35±0.04 (manual) (P<0.05).

CONCLUSION: In this laboratory pig-eye study, femtosecond laser-assisted capsulotomy resulted in a significantly stronger anterior capsule opening than the standard manually performed capsulotomy.

Source: J. Cataract Refract. Surg. 2013; 39:105-109 Q 2013 ASCRS and ESCRS.

A very accurate positioning of an opening 32 in a capsular bag 22, and a very accurately shape of the opening 32, allow an accurate positioning and orientation of the IOL 1 described, and are in particular advantageous when using the current IOL or IOL/S-IOL combination.

The IOL 1 can be used in the following way. Often, the IOL 1 is inserted in the capsular bag via a micro incision in the eye. Via an insertion device, the IOL outside the eye is rolled up and urged forward through a nozzle that fits through the incision in the eye. The rolled-up IOL 1 enters the capsular bag via the opening. The rolled-up IOL 1 unfolds inside the capsular bag.

Next, using a small tool, the anterior supports 6, 6' are manipulated to fold back through the opening 32 in the anterior capsular bag part 23 to extend outside the capsular bag 22. Using the same or an identical tool, the lips 8, 8' may be manipulated to also extend through the opening 32 and to reach out of the capsular bag 22. The posterior surfaces 17 and 17' of the lips 8, 8' will then rest on the anterior surface of the anterior part 23 of the capsular bag 22. If the posterior capsule is opened as well then in a second manoeuvre by gently pushing the IOL a little bit downward the posterior flap will be secured in the posterior groove 12.

Figure 13:
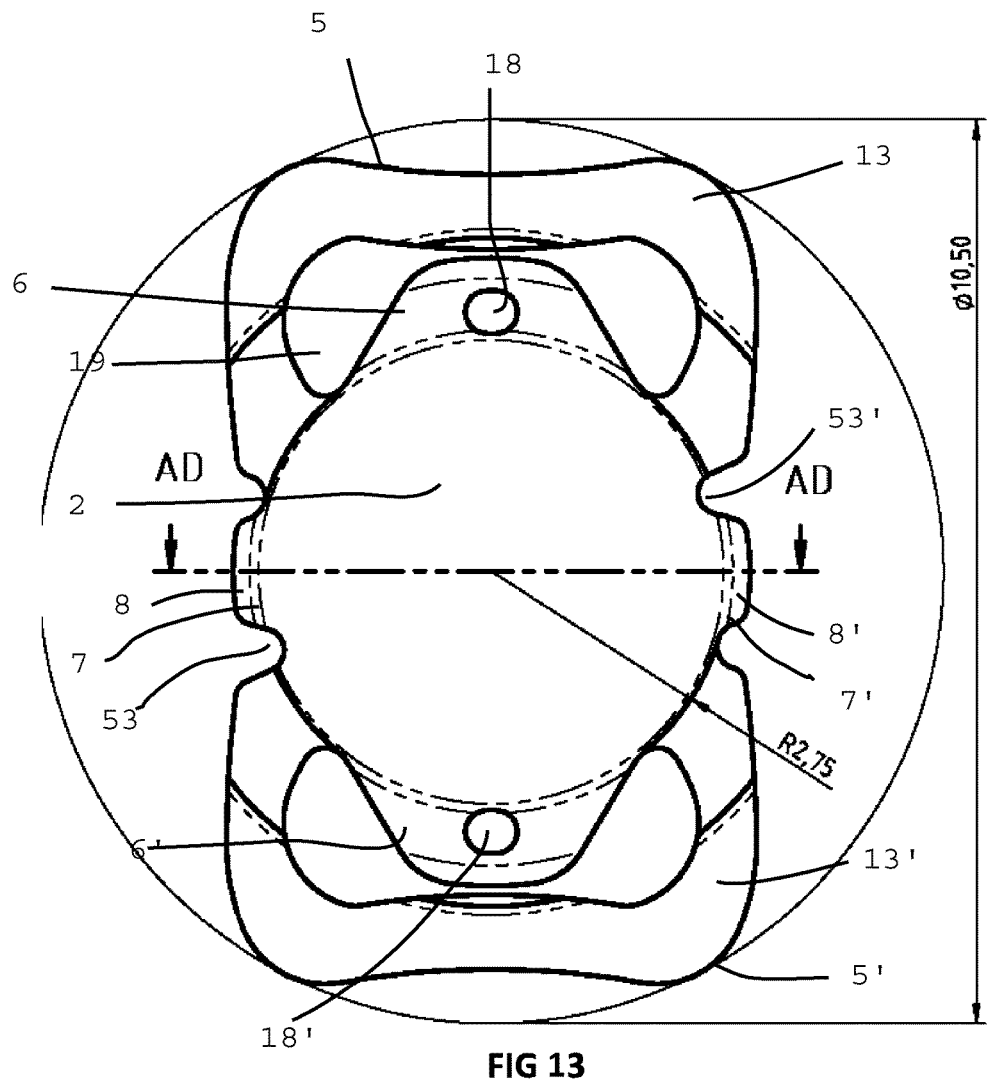

In FIGS. 13 and 14, an alternative embodiment of the IOL 1 of FIG. 8 is shown. In FIG. 13, the embodiment of FIG. 14 is shown partly from the rear in perspective. Again, similar reference numbers show similar elements.

Capsular bag distension syndrome (CBDS) is an uncommon, but well recognized cause of reduced vision following cataract surgery. It usually presents in the immediate post-operative period, with shallowing of the anterior chamber, unexpected myopic refraction and accumulation of liquefied substance between the implanted lens and posterior capsule.

The most likely mechanism of CBDS is the production of collagens from residual lens epithelial cells or necrotic and/or apoptotic autolyzed lens epithelial cells or the retained viscoelastic from the surgical procedure accumulates behind the intraocular lens (IOL) as the IOL optic occludes the anterior capsular opening made by the capsulotomy. The creation of a small opening in the lens to avoid total sealing of the bag may avoid this post-operative complication. The opening could be shaped in the form of notch at the optic edge or a small hole made in the optic. It is also possible to create small capsulotomies when the capsule opening is made in the anterior or posterior capsule flaps to avoid complete sealing of the capsular opening when using the IOL described earlier.

In the embodiment of FIG. 13 an 14, another approach is chosen. In this embodiment, an indentation 53 is created in the peripheral surface 7. This indentation 53 provides an axial (Ax) groove in the perimeter 7 about the IOL. Here, the groove as straight in axial (Ax) direction, but amendments may be made to control flow of fluid. This indentation 53 creates a passage between the peripheral surface 7 and the edge 52 of the opening 32 in the anterior part of the capsular bag 23 after insertion of the IOL 1. Thus, a passage for fluid is provided once the IOL is inserted in the opening 32 in the capsular bag. In fact, even if the posterior groove 12 is provided in the IOL, this groove may provide a passage for fluid part once the posterior part of the capsular bag is inserted in the posterior groove 12. In fact, the radial extension of the indentation may control such a passage.

In order to provide an easy passage, the indentation 53 is provided in radial sense next to a posterior support 5, 5' or an anterior support 6, 6'. In the embodiment shown in the drawings, the indentation 53 is provided between a posterior support 5, 5' and an anterior support 6, 6'. In this embodiment, two indentations 53 are provided, here opposite one another. Here, the diameter of the indentations 53 are selected to allow eye fluid to pass the passage. In this embodiment, the width of the indentations 53 is here 0.2-0.6 mm. In particular, the width is 0.25-0.5 mm. The depth of the indentations 53 is here 0.05-0.4 mm. In particular, the depth is 0.1-0.3 mm.

In FIGS. 15-18 a perspective view, view of a detail, a front and rear view, respectively, of an alternative embodiment of the IOL. Again, identical reference numbers refer to features that are at least functionally equivalent. More in particular, in this embodiment the indentation 53 was modified. In this embodiment, the position (in circumferential or tangential sense T) of the indentations 53 is adapted. Furthermore here three indentations 53 are provided. It was found that the indentations 53 resulted in an interruption of the posterior rim 16. As already explained, the posterior side of the IOL 1 at and near the perimeter is provided with a sharp rim 16 to prevent growth of tissue from the posterior capsular bag part. Such growth of tissue can cause posterior capsular opacification. The indentations 53 of the earlier embodiment of FIGS. 13 and 14 interrupt that rim 16, thus presenting a risk of growth of tissue which may start posterior capsular opasification. This tissue may for instance block the indentation, preventing exchange of fluids.

Figure 15:
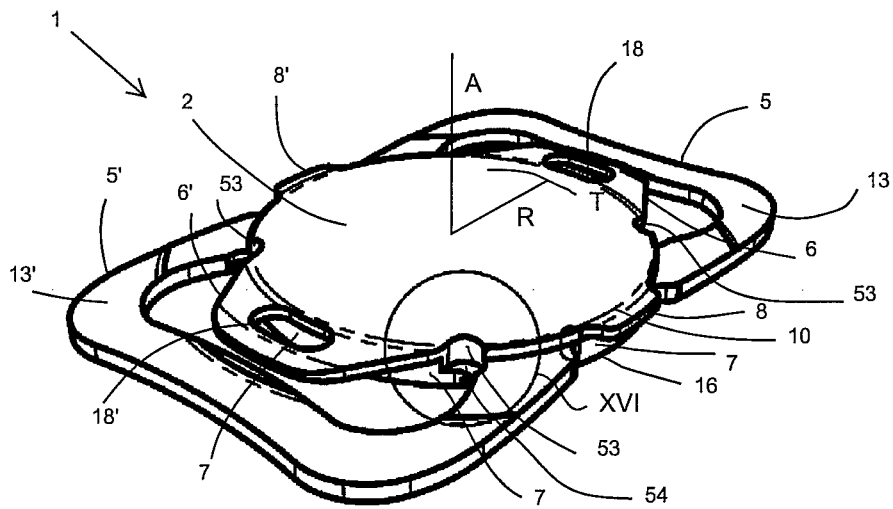
FIGS. 15-18 a perspective view, view of a detail, a front and rear view, respectively, of an alternative embodiment of the IOL.
Figure 16:
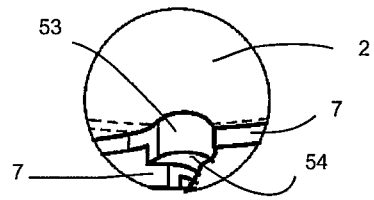
Figures 17, 18:
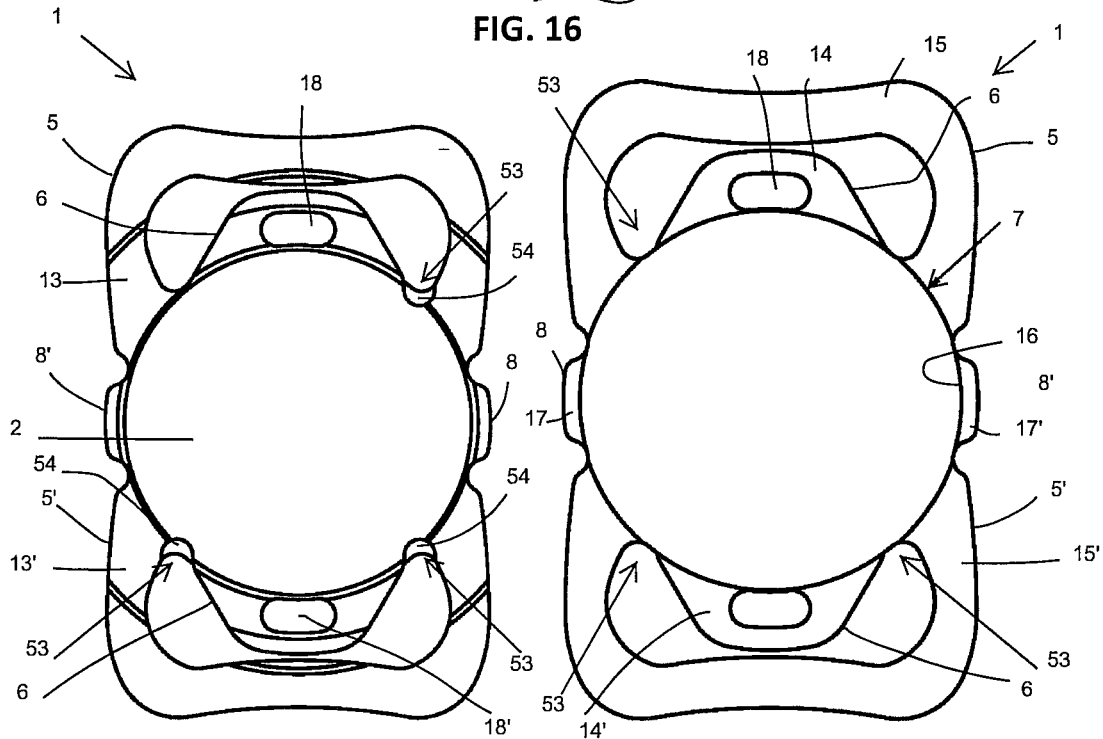
Figures 19A, 19B:
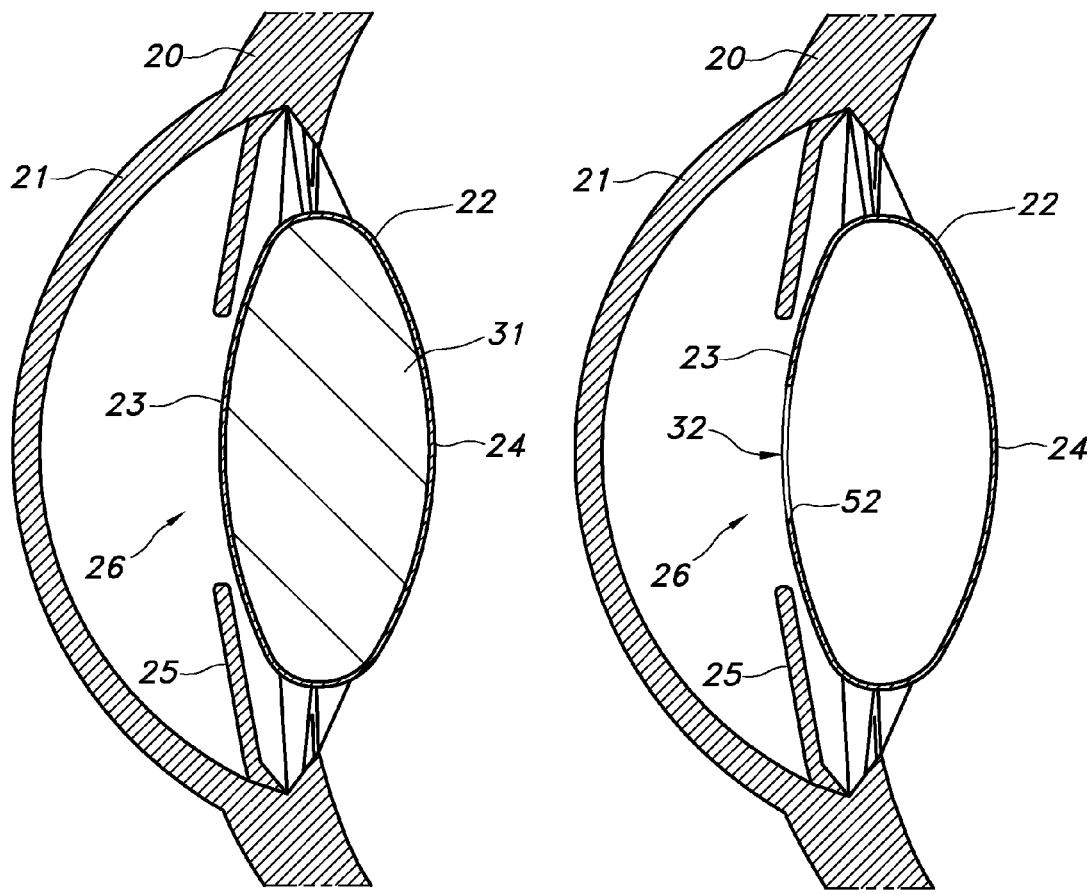
Figure 19C:
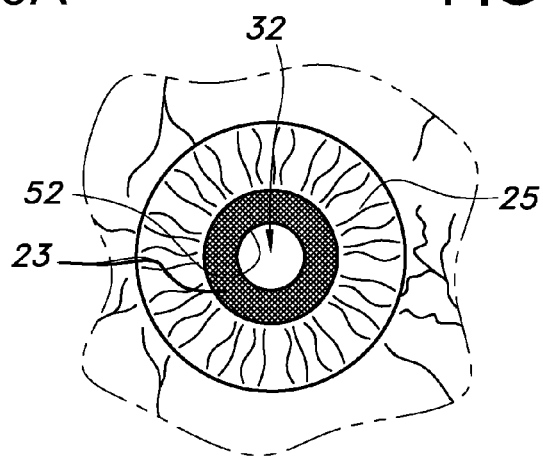

Here, the indentation opens at the anterior side of the IOL. The depth (in axial direction A, for clarity reasons also the radial direction R is indicated in FIG. 15) is selected that the indentation extends past the edge 52 of the capsular bag once the IOL 1 is implanted. In practice, the indentation in axial direction A extends beyond the posterior surface 14, 14' of the anterior supports 6, 6'. In an embodiment, the indentation extends beyond the anterior surface 13, 13' of the posterior supports 5, 5'. Thus, the indentations provide a fluid channel past the capsular bag 23. The indentations 53 here end before the posterior rim 16, leaving its edge in tact. Thus, the indentations 53 have a bottom or end 54. The indentations 53 extend radially R inward with respect to the peripheral surface 7. The supports 5, 5', 6, 6' extend radially outward from the peripheral surface 7. Before implantation, in an embodiment, the posterior surface of the anterior supports 6, 6' in an embodiment in radial direction R extends past the peripheral surface 7. The anterior surface of the posterior supports 5, 5' in an embodiment in radial direction R extends past the peripheral surface 7 in opposite direction. Thus, the supports can clamp the capsular bag between them.

FIGS. 20-25 show various other embodiments of an IOL allowing easier production, and easier implantation and fixation in an eye.

Figure 20:
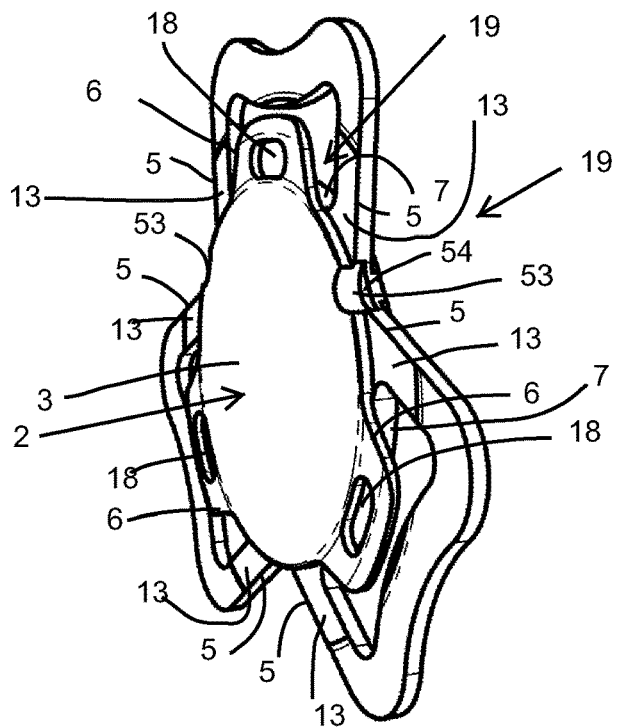
FIGS. 20-21 a further embodiment of an IOL in perspective view and in front view looking on the anterior side of the IOL.
Figure 21:
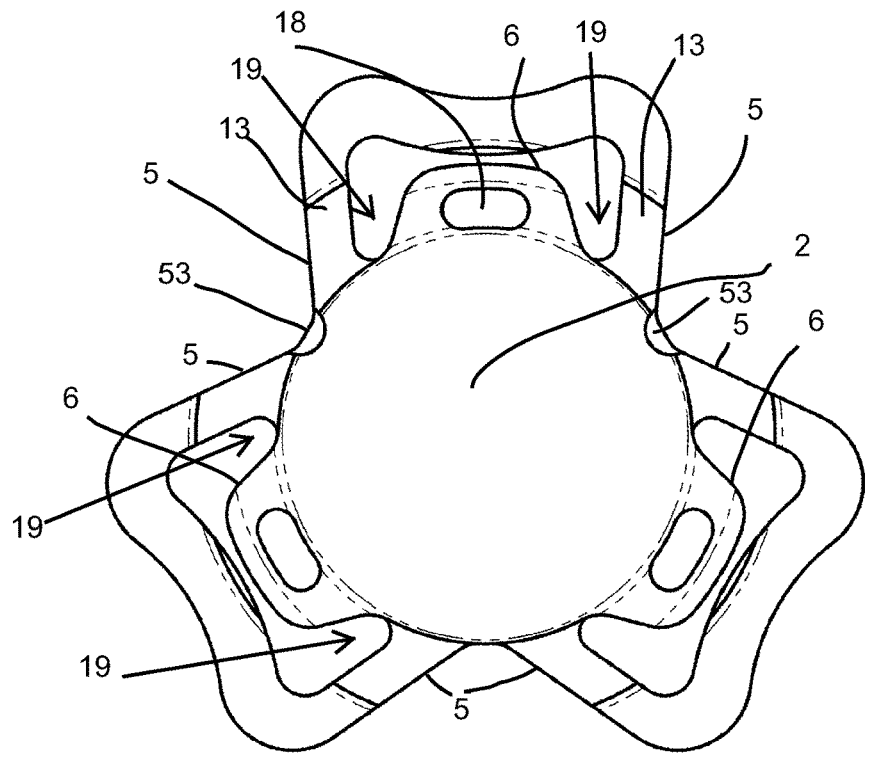

In these embodiments these are multiple posterior supports and multiple anterior supports. They are not separately indicated with an '-mark. The same parts or features again have the same references and will not be discussed further. FIG. 20 shows a perspective view and FIG. 21 shows a view from the anterior, showing the anterior side of the IOL.

There, the IOL has three haptics remaining in the (remainder of) the capsular bag. The haptics provide in fact six posterior supports 5 which are two by two coupled at their radial ends. They extend further in radial (Ra) direction then the anterior supports 6. When viewed like in FIG. 21, it is clear that the supports 5, 6 do not overlap. The through holed 18 in the anterior supports 6 again allows the anterior supports 6 to be brought out of the capsular bag easily. This can provide better centering in the capsular bag.

Figure 22:
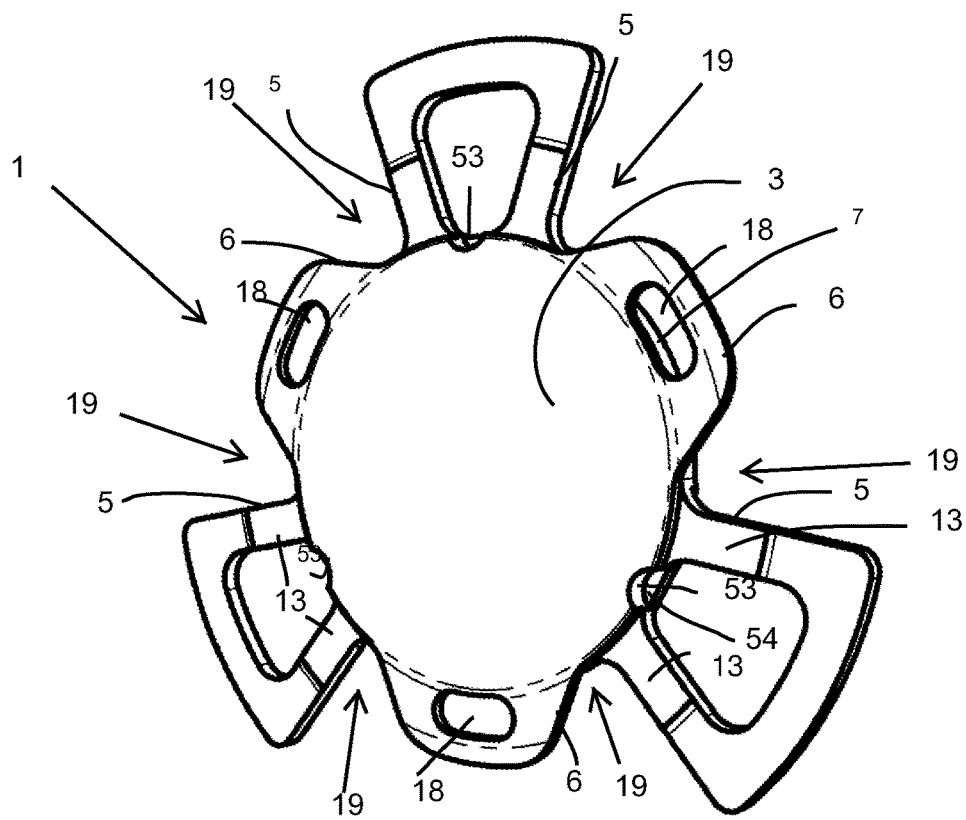
FIGS. 22-23 yet another embodiment of an IOL in perspective view and in front view looking on the anterior side of the IOL, and FIGS. 24-25 yet another embodiment of an IOL in perspective view and in front view looking on the anterior side of the IOL.
Figure 23:
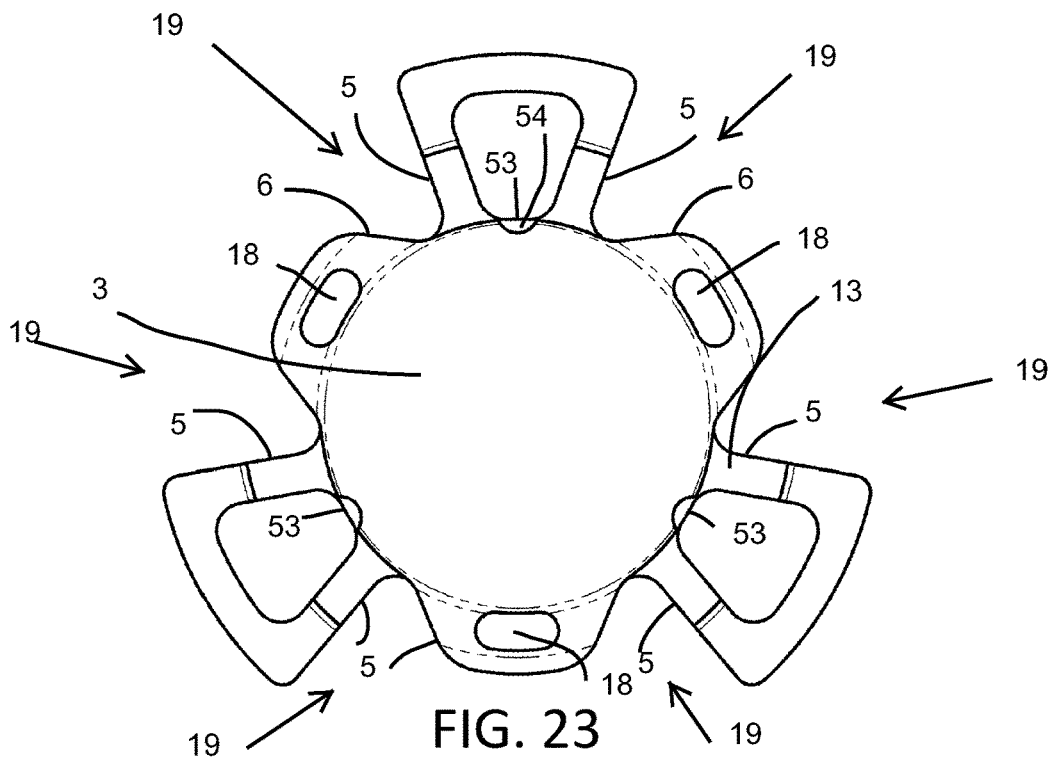

In the embodiment of FIGS. 22 and 23, the bottom 54 of the axial indentations 53 are further remote to the posterior direction then the anterior surfaces 13 of the posterior supports. This provides a more sure fluid channel. The axial indentations 53 in the perimeter 7 (also referred to as axial groove 53) may also taper in posterior direction. This may make tooling or moulding such a lens easier.

Again, the two-by-two connected posterior supports 5 may also provide the functionality of haptics. Another definition may be that there are three posterior supports that have through openings. The posterior supports 5 and anterior supports 6 again do not overlap. They are azimuthally shifted.

Figure 24:
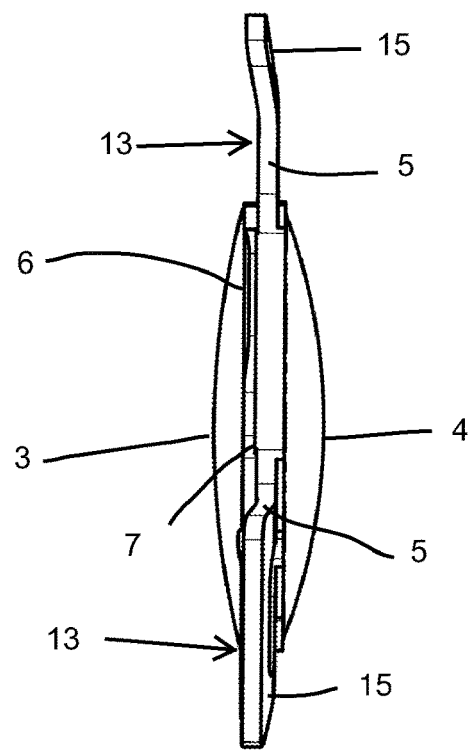
Figure 25:
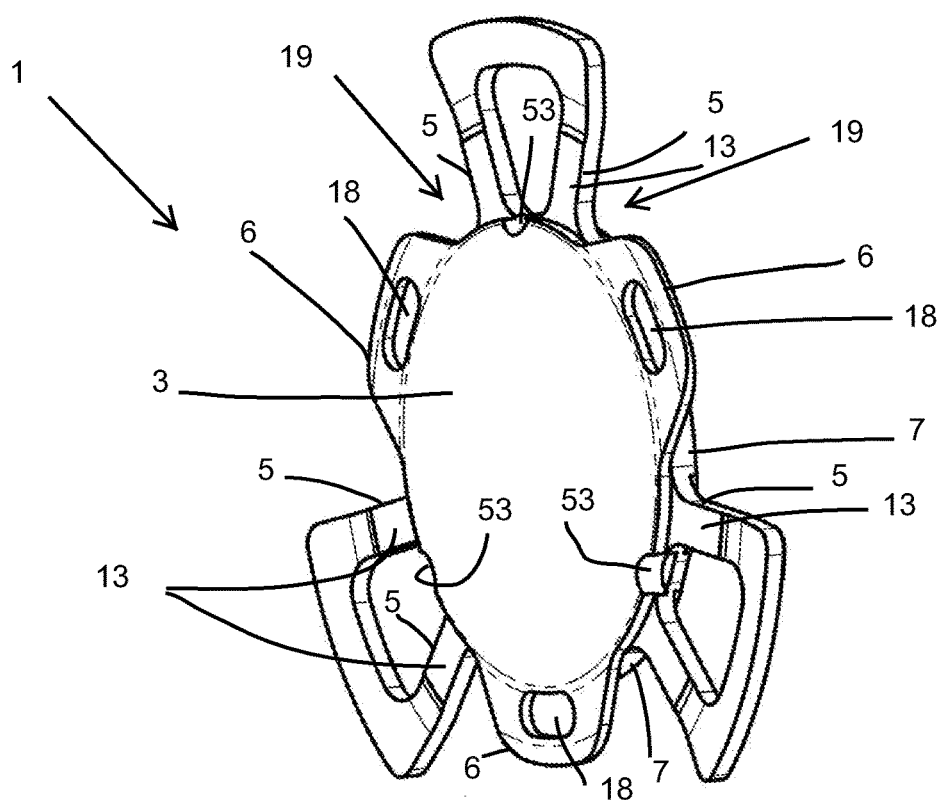

The embodiment of FIGS. 24 and 25 differs little from the embodiment of FIGS. 22 and 23. In this embodiment, the posterior supports 5 are angulated in anterior direction. Thus, part of their posterior surface 15 is visible in the side view of FIG. 24. Thus in some cases, fixation in the capsular bag may be improved. In the embodiment with angulation in anterior direction, the lens is pressed a little in posterior direction, and may rest against the posterior capsular bag part. Pressing more secure to the capsule may prevent posterior capsule opacification. When a through hole is also provided in the posterior capsular bag part, as explained earlier, fixation in that hole may improve.

It will also be clear that the above description and drawings are included to illustrate some embodiments of the invention, and not to limit the scope of protection. Starting from this disclosure, many more embodiments will be evident to a skilled person. These embodiments are within the scope of protection and the essence of this invention and are obvious combinations of prior art techniques and the disclosure of this patent.

LIST OF REFERENCE NUMBERS

1 Intra ocular lens structure (IOL)
2 Optical structure
3 Anterior surface of the IOL
4 Posterior surface of the IOL
5, 5' Posterior supports
6, 6' Anterior supports
7 perimeter of the IOL
8, 8' Additional anterior lips
9 Outer perimeter of the optical structure
10 Perimeter of the optical structure
11 Space between the posterior plane and anterior plane
12 Posterior groove for the posterior capsular bag flap
13, 13' Anterior support surfaces of the posterior support
14, 14' posterior support surfaces of the anterior support
15 15' Posterior surfaces of the posterior support
16 Posterior rim
17, 17' Posterior surfaces of the additional anterior lips
18, 18' holes in the anterior support
19 azimuthal (Az) space between posterior and anterior supports
20 eyeball
21 Cornea
22 Capsular bag
23 Anterior part of the capsular bag
24 Posterior part of the capsular bag
25 Iris
26 pupil
31 natural lens
32 opening (in the anterior part of the capsular bag)
47 optical axis
48 fovea
49 pupillary axis
50 line of sight
51 visual axis
52 perimetrical edge of the anterior capsular bag flap
53 Indentation
54 end of indentation

The invention claimed is:

1. An intra ocular lens structure (IOL) for placement in the capsular bag and securing the IOL in an opening in an anterior part of a capsular bag, with an anterior capsular bag flap surrounding said opening, said IOL having an anterior side which in use when the IOL is implanted in capsular bag of an eye is directed towards a cornea of the eye, and a posterior side which in use when the IOL is implanted in an eye is directed towards a retina of the eye, said IOL comprising:
an optical structure comprising a perimeter;
at least two posterior supports, coupled to and extending away from said perimeter of said optical structure, said posterior supports adapted for in use providing support surfaces for engaging a posterior surface of an anterior capsular bag flap, said posterior supports residing inside the capsular bag when the IOL is implanted in the capsular bag, and—at least two anterior supports, coupled to and extending from said perimeter of said optical structure, for residing outside the capsular bag and extending away from said optical structure, said anterior supports adapted for in use providing support surfaces for engaging an anterior surface of an anterior capsular bag flap, wherein a posterior plane defined by the support surfaces of the posterior supports and an anterior plane defined by the support surfaces of the anterior supports are adapted for in use being spaced apart at a distance adapted for holding an anterior capsular bag flap between them for securing the IOL in said opening, wherein said posterior supports and said anterior supports are in perimetrical sense or azimuthal direction shifted with respect to one another.

2. The IOL of claim 1, wherein when the IOL is implanted in the capsular bag, the anterior supports and the posterior supports are mutually positioned on said perimeter for holding an anterior capsular bag flap between them for securing the IOL in said opening in an anterior part of a capsular bag.

3. The IOL of claim 1, wherein said at least two posterior supports extend away from said optical structure in a functionally opposite direction with respect to one another, and said at least two anterior supports extending away from said optical structure in a functionally opposite direction with respect to one another.

4. The IOL of claim 1, wherein said anterior plane and said posterior plane are spaced apart 5 to 70 micron, in particular wherein said posterior and anterior planes are spaced apart 5-50 micron.

5. The IOL of claim 1, wherein said posterior supports and said anterior supports extend in perimetrical direction or in azimuthal sense about the optical structure.

6. The IOL of claim 1, wherein the posterior supports and the anterior supports functionally do not overlap, in particularly do not overlap.

7. The IOL of claim 1, wherein said IOL comprises a perimetrical surface surrounding said optical structure and said posterior support and said anterior support extending from said perimetrical surface, said perimetrical surface defining a radial surface for when said IOL is implanted engaging a perimetrical edge of the anterior capsular bag flap which defines the perimeter of the opening.

8. The IOL of claim 1, wherein said anterior supports comprise through holes or openings.

9. The IOL of claim 1, wherein—said at least two posterior supports comprise closed loops which extend from said optical structure, and each loop has both ends attached to said perimeter, and—said at least two anterior supports are each positioned within one of said loops between said ends.

10. The IOL according to claim 1, wherein said posterior supports and said anterior supports of the IOL are in azimuthal sense (Az) shifted or staggered with respect to one another.

11. The IOL according to claim 1, wherein said IOL is formed in one piece, its thickness and flexibility adapted for insertion of the IOL into the eye in a folded manner via a micro insertion.

12. The IOL according to claim 1, further comprising an at least partially perimetrical groove posterior to the posterior supports, in particular said posterior groove opening in a radial direction for receiving, when said IOL is implanted in an eye, at least an edge of a posterior capsular bag flap surrounding a posterior opening in a posterior part of the capsular bag.

13. The IOL of claim 12, wherein said posterior groove is between 0.1 and 0.3 mm deep, in particular said posterior groove is between 0.05-0.2 mm wide, more in particular said posterior groove is tapered.

14. The IOL according to claim 1, wherein said support surfaces are in azimuthal sense (Az) shifted or staggered with respect to one another, in particular providing in azimuthal sense (Az) each time a support surface and an anterior support surface.

15. The IOL according to claim 1, wherein said posterior supports and said anterior supports of the IOL extend in azimuthal sense (Az) about the optical structure.

16. The IOL according to claim 1, wherein said IOL comprises an indentation in said perimeter, providing an axially (A) extending groove in the peripheral surface of said perimeter.

* * * * *